(12) United States Patent
Specht et al.

(10) Patent No.: US 10,653,392 B2
(45) Date of Patent: May 19, 2020

(54) ULTRASOUND IMAGING USING APPARENT POINT-SOURCE TRANSMIT TRANSDUCER

(71) Applicant: MAUI IMAGING, INC., San Jose, CA (US)

(72) Inventors: Donald F. Specht, Los Altos, CA (US); Josef R. Call, Campbell, CA (US)

(73) Assignee: MAUI IMAGING, INC., San Jose, CA (US)

( * ) Notice: Subject to any disclaimer, the term of this patent is extended or adjusted under 35 U.S.C. 154(b) by 0 days.

(21) Appl. No.: 16/137,221

(22) Filed: Sep. 20, 2018

(65) Prior Publication Data

US 2019/0021697 A1 Jan. 24, 2019

Related U.S. Application Data

(60) Continuation of application No. 15/888,738, filed on Feb. 5, 2018, now abandoned, which is a division of
(Continued)

(51) Int. Cl.
*A61B 8/00* (2006.01)
*G01S 15/89* (2006.01)
(Continued)

(52) U.S. Cl.
CPC ........ *A61B 8/4483* (2013.01); *G01S 7/52077* (2013.01); *G01S 7/52079* (2013.01);
(Continued)

(58) Field of Classification Search
CPC ... A61B 8/4483; A61B 8/4461; A61B 8/5207; A61B 8/483; G01S 15/8995;
(Continued)

(56) References Cited

U.S. PATENT DOCUMENTS 3,174,286 A 3/1965 Erickson
3,895,381 A 7/1975 Kock
(Continued)

FOREIGN PATENT DOCUMENTS

CN 1535243 A 10/2004
CN 1781460 A 6/2006
(Continued)

OTHER PUBLICATIONS

Abeysekera et al.; Alignment and calibration of dual ultrasound transducers using a wedge phantom; Ultrasound in Medicine and Biology; 37(2); pp. 271-279; Feb. 2011.
(Continued)

*Primary Examiner* — Bo Joseph Peng
(74) *Attorney, Agent, or Firm* — Shay Glenn LLP

(57) ABSTRACT

An apparent point-source transmit transducers comprises a substantially constant-thickness shell of piezoelectric material in a shape of a spherical-section. Such transducers may be sized such that a single apparent point-source transmit transducer may produce ultrasound waveforms with substantial energy in a medium to be imaged. Use of such transducers in three-dimensional ping-based imaging may permit deeper and higher quality imaging than may be possible with conventional transducers.

13 Claims, 11 Drawing Sheets

Related U.S. Application Data application No. 14/279,052, filed on May 15, 2014, now Pat. No. 9,883,848.

(60) Provisional application No. 61/877,555, filed on Sep. 13, 2013.

(51) Int. Cl.
*G01S 7/52* (2006.01)
*A61B 8/08* (2006.01)

(52) U.S. Cl.
CPC ...... *G01S 15/8913* (2013.01); *G01S 15/8915* (2013.01); *G01S 15/8929* (2013.01); *G01S 15/8993* (2013.01); *G01S 15/8997* (2013.01); *A61B 8/4461* (2013.01); *A61B 8/483* (2013.01); *A61B 8/5207* (2013.01); *G01S 15/8995* (2013.01)

(58) Field of Classification Search
CPC ............. G01S 15/8997; G01S 15/8993; G01S 15/8913; G01S 15/8915; G01S 15/8929; G01S 7/52079; G01S 7/52077
See application file for complete search history.

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,205,394 A | 5/1980 | Pickens |
| 4,229,798 A | 10/1980 | Rosie |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,694,434 A | 9/1987 | Vonn Ramm et al. |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 4,990,462 A | 2/1991 | Sliwa, Jr. |
| 5,050,588 A | 9/1991 | Grey et al. |
| 5,062,295 A | 11/1991 | Shakkottai et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,340,510 A | 8/1994 | Bowen |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tei et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,625,149 A | 4/1997 | Gururaja et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,951,479 A | 9/1999 | Holm et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,222,304 B1 | 4/2001 | Bernstein |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |

(56) References Cited

U.S. PATENT DOCUMENTS

| | | |
|---|---|---|
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,370,480 B1 | 4/2002 | Gupta et al. |
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,597,171 B2 | 7/2003 | Hurlimann et al. |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,704,692 B1 | 3/2004 | Banerjee et al. |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,835,178 B1 | 12/2004 | Wilson et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 | 3/2005 | Thomenius et al. |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 | 11/2007 | Lee et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,764,984 B2 | 7/2010 | Desmedt et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,880,154 B2 | 2/2011 | Otto |
| 7,887,486 B2 | 2/2011 | Ustuner et al. |
| 7,901,358 B2 | 3/2011 | Mehi et al. |
| 7,914,451 B2 | 3/2011 | Davies |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 8,265,175 B2 | 9/2012 | Barsoum et al. |
| 8,277,383 B2 | 10/2012 | Specht |
| 8,279,705 B2 | 10/2012 | Choi et al. |
| 8,412,307 B2 | 4/2013 | Willis et al. |
| 8,414,564 B2 | 4/2013 | Goldshleger et al. |
| 8,419,642 B2 | 4/2013 | Sandrin et al. |
| 8,473,239 B2 | 6/2013 | Specht et al. |
| 8,478,382 B2 | 7/2013 | Burnside et al. |
| 8,483,804 B2 | 7/2013 | Hsieh et al. |
| 8,532,951 B2 | 9/2013 | Roy et al. |
| 8,582,848 B2 | 11/2013 | Funka-Lea et al. |
| 8,602,993 B2 | 12/2013 | Specht et al. |
| 8,627,724 B2 | 1/2014 | Papadopoulos et al. |
| 8,634,615 B2 | 1/2014 | Brabec |
| 8,672,846 B2 | 3/2014 | Napolitano et al. |
| 8,684,936 B2 | 4/2014 | Specht |
| 9,036,887 B2 | 5/2015 | Fouras et al. |
| 9,072,495 B2 | 7/2015 | Specht |
| 9,146,313 B2 | 9/2015 | Specht et al. |

(56) References Cited

U.S. PATENT DOCUMENTS

| | | |
|---|---|---|
| 9,152,761 B2 | 10/2015 | Bhatia et al. |
| 9,176,078 B2 | 11/2015 | Flohr et al. |
| 9,192,355 B2 | 11/2015 | Specht et al. |
| 9,217,660 B2 | 12/2015 | Zlotnick et al. |
| 9,220,478 B2 | 12/2015 | Smith et al. |
| 9,247,874 B2 | 2/2016 | Kumar et al. |
| 9,247,926 B2 | 2/2016 | Smith et al. |
| 9,265,484 B2 | 2/2016 | Brewer et al. |
| 9,268,777 B2 | 2/2016 | Lu et al. |
| 9,271,661 B2 | 3/2016 | Moghari et al. |
| 9,277,861 B2 | 3/2016 | Kowal et al. |
| 9,282,945 B2 | 3/2016 | Smith et al. |
| 9,339,239 B2 | 5/2016 | Wang et al. |
| 9,339,256 B2 | 5/2016 | Specht et al. |
| 9,392,986 B2 | 7/2016 | Ning et al. |
| 9,420,994 B2 | 8/2016 | Specht |
| 9,510,806 B2 | 12/2016 | Smith et al. |
| 9,526,475 B2 | 12/2016 | Specht et al. |
| 9,526,485 B2 | 12/2016 | Yang |
| 9,572,549 B2 | 2/2017 | Belevich et al. |
| 9,576,354 B2 | 2/2017 | Fouras et al. |
| 9,582,876 B2 | 2/2017 | Specht |
| 9,606,206 B2 | 3/2017 | Boernert et al. |
| 9,659,152 B2 | 5/2017 | Mueller |
| 9,668,714 B2 | 6/2017 | Call et al. |
| 9,775,511 B2 | 10/2017 | Kumar et al. |
| 9,788,813 B2 | 10/2017 | Adam et al. |
| 9,883,848 B2 | 2/2018 | Specht et al. |
| 9,901,407 B2 | 2/2018 | Breisacher et al. |
| 9,986,975 B2 | 6/2018 | Specht et al. |
| 10,064,605 B2 | 9/2018 | Belevich et al. |
| 10,130,333 B2 | 11/2018 | Specht |
| 10,206,662 B2 | 2/2019 | Smith et al. |
| 10,226,234 B2 | 3/2019 | Specht et al. |
| 10,267,913 B2 | 4/2019 | Smith et al. |
| 10,342,518 B2 | 7/2019 | Specht et al. |
| 10,380,399 B2 | 8/2019 | Call et al. |
| 10,401,493 B2 | 9/2019 | Call et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0015079 A1 | 1/2004 | Berger et al. |
| 2004/0054283 A1 | 3/2004 | Corey et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0215075 A1 | 10/2004 | Zagzebski et al. |
| 2004/0236217 A1 | 11/2004 | Cerwin et al. |
| 2004/0236223 A1 | 11/2004 | Barnes et al. |
| 2004/0267132 A1 | 12/2004 | Podany |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0061536 A1 | 3/2005 | Proulx |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0058664 A1 | 3/2006 | Barthe et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262961 A1 | 11/2006 | Holsing et al. |
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0073781 A1 | 3/2007 | Adkins et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0015665 A1 | 1/2009 | Willsie |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |

(56) References Cited

U.S. PATENT DOCUMENTS

| | | |
|---|---|---|
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0079299 A1 | 3/2009 | Bradley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182233 A1 | 7/2009 | Wodnicki |
| 2009/0182237 A1 | 7/2009 | Angelsen et al. |
| 2009/0198134 A1 | 8/2009 | Hashimoto et al. |
| 2009/0199392 A1 | 8/2009 | Singh et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0036258 A1 | 2/2010 | Dietz et al. |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0085383 A1 | 4/2010 | Cohen et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0145195 A1 | 6/2010 | Hyun |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0174198 A1 | 7/2010 | Young et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0317971 A1 | 12/2010 | Fan et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178441 A1 | 7/2011 | Tyler |
| 2011/0270088 A1 | 11/2011 | Shiina |
| 2011/0301470 A1 | 12/2011 | Sato et al. |
| 2011/0306886 A1 | 12/2011 | Daft et al. |
| 2011/0319764 A1 | 12/2011 | Okada et al. |
| 2012/0004545 A1 | 1/2012 | Ziv-Ari et al. |
| 2012/0035482 A1 | 2/2012 | Kim et al. |
| 2012/0036934 A1 | 2/2012 | Kröning et al. |
| 2012/0085173 A1 | 4/2012 | Papadopoulos et al. |
| 2012/0101378 A1 | 4/2012 | Lee |
| 2012/0114210 A1 | 5/2012 | Kim et al. |
| 2012/0121150 A1 | 5/2012 | Murashita |
| 2012/0137778 A1 | 6/2012 | Kitazawa et al. |
| 2012/0140595 A1 | 6/2012 | Amemiya |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0235998 A1 | 9/2012 | Smith-Casem et al. |
| 2012/0243763 A1 | 9/2012 | Wen et al. |
| 2012/0253194 A1 | 10/2012 | Tamura |
| 2012/0265075 A1 | 10/2012 | Pedrizzetti et al. |
| 2012/0277585 A1 | 11/2012 | Koenig et al. |
| 2013/0070062 A1 | 3/2013 | Fouras et al. |
| 2013/0076207 A1 | 3/2013 | Krohn et al. |
| 2013/0079639 A1 | 3/2013 | Hoctor et al. |
| 2013/0083628 A1 | 4/2013 | Qiao et al. |
| 2013/0088122 A1 | 4/2013 | Krohn et al. |
| 2013/0116561 A1 | 5/2013 | Rothberg et al. |
| 2013/0131516 A1 | 5/2013 | Katsuyama |
| 2013/0144165 A1 | 6/2013 | Ebbini et al. |
| 2013/0204136 A1 | 8/2013 | Duric et al. |
| 2013/0204137 A1 | 8/2013 | Roy et al. |
| 2013/0258805 A1 | 10/2013 | Hansen et al. |
| 2013/0261463 A1 | 10/2013 | Chiang et al. |
| 2014/0058266 A1* | 2/2014 | Call .................. A61B 8/14 600/448 |
| 2014/0073921 A1 | 3/2014 | Specht et al. |
| 2014/0086014 A1 | 3/2014 | Kobayashi |
| 2014/0147013 A1 | 5/2014 | Shandas et al. |
| 2014/0243673 A1 | 8/2014 | Anand et al. |
| 2015/0045668 A1 | 2/2015 | Smith et al. |
| 2015/0172878 A1 | 6/2015 | Luna et al. |
| 2016/0095579 A1 | 4/2016 | Smith et al. |
| 2016/0135783 A1 | 5/2016 | Brewer et al. |
| 2016/0256134 A1 | 9/2016 | Specht et al. |
| 2017/0209121 A1 | 7/2017 | Davies et al. |
| 2017/0224312 A1 | 8/2017 | Call et al. |
| 2018/0049717 A1 | 2/2018 | Adam et al. |
| 2018/0153511 A1 | 6/2018 | Specht et al. |
| 2018/0279991 A1 | 10/2018 | Call et al. |
| 2019/0008487 A1 | 1/2019 | Belevich et al. |
| 2019/0083058 A1 | 3/2019 | Specht |
| 2019/0175152 A1 | 6/2019 | Smith et al. |
| 2019/0200961 A1 | 7/2019 | Specht et al. |
| 2019/0328367 A1 | 10/2019 | Specht et al. |
| 2019/0370522 A1 | 12/2019 | Call et al. |

FOREIGN PATENT DOCUMENTS

| | | |
|---|---|---|
| CN | 101103927 A | 1/2008 |
| CN | 101116622 A | 2/2008 |
| CN | 101190134 A | 6/2008 |
| CN | 101453955 A | 6/2009 |
| CN | 100545650 C | 9/2009 |
| CN | 101609150 A | 12/2009 |
| CN | 101843501 A | 9/2010 |
| CN | 101912278 A | 12/2010 |
| CN | 102018533 A | 4/2011 |
| CN | 102112047 A | 6/2011 |
| CN | 102123668 A | 7/2011 |
| CN | 102599930 A | 7/2012 |
| DE | 102011114333 A1 | 3/2013 |
| EP | 1949856 A1 | 7/2008 |
| EP | 2058796 A2 | 5/2009 |
| EP | 2101191 A2 | 9/2009 |
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 1462819 B1 | 7/2011 |
| EP | 2356941 A1 | 8/2011 |
| EP | 1979739 B1 | 10/2011 |
| EP | 2385391 A2 | 11/2011 |
| EP | 2294400 B1 | 2/2012 |
| EP | 2453256 A2 | 5/2012 |
| EP | 1840594 B1 | 6/2012 |

(56) References Cited

FOREIGN PATENT DOCUMENTS

| | | |
|---|---|---|
| EP | 2514368 A1 | 10/2012 |
| EP | 1850743 B1 | 12/2012 |
| EP | 1594404 B1 | 9/2013 |
| EP | 2026280 B1 | 10/2013 |
| FR | 2851662 A1 | 8/2004 |
| JP | 49-11189 A | 1/1974 |
| JP | 54-44375 A | 4/1979 |
| JP | 55-103839 A | 8/1980 |
| JP | 57-31848 A | 2/1982 |
| JP | 58-223059 A | 12/1983 |
| JP | 59-101143 A | 6/1984 |
| JP | 59-174151 A | 10/1984 |
| JP | 60-13109 U | 1/1985 |
| JP | 60-68836 A | 4/1985 |
| JP | 01164354 A | 6/1989 |
| JP | 02501431 A | 5/1990 |
| JP | 03015455 A | 1/1991 |
| JP | 03126443 A | 5/1991 |
| JP | 04017842 A | 1/1992 |
| JP | 04067856 A | 3/1992 |
| JP | 05042138 A | 2/1993 |
| JP | 06125908 A | 5/1994 |
| JP | 06254092 A | 9/1994 |
| JP | 07051266 A | 2/1995 |
| JP | 07204201 A | 8/1995 |
| JP | 08154930 A | 6/1996 |
| JP | 08252253 A | 10/1996 |
| JP | 09103429 A | 4/1997 |
| JP | 09201361 A | 8/1997 |
| JP | 2777197 B | 5/1998 |
| JP | 10216128 A | 8/1998 |
| JP | 11089833 A | 4/1999 |
| JP | 11239578 A | 9/1999 |
| JP | 2001507794 A | 6/2001 |
| JP | 2001245884 A | 9/2001 |
| JP | 2002209894 A | 7/2002 |
| JP | 2002253548 A | 9/2002 |
| JP | 2002253549 A | 9/2002 |
| JP | 2003235839 A | 8/2003 |
| JP | 2004167092 A | 6/2004 |
| JP | 2004215987 A | 8/2004 |
| JP | 2004337457 A | 12/2004 |
| JP | 2004340809 A | 12/2004 |
| JP | 2004351214 A | 12/2004 |
| JP | 2005046192 A | 2/2005 |
| JP | 2005152187 A | 6/2005 |
| JP | 2005523792 A | 8/2005 |
| JP | 2005526539 A | 9/2005 |
| JP | 2006051356 A | 2/2006 |
| JP | 2006061203 A | 3/2006 |
| JP | 2006122657 A | 5/2006 |
| JP | 2006130313 A | 5/2006 |
| JP | 2006204923 A | 8/2006 |
| JP | 2007325937 A | 12/2007 |
| JP | 2008122209 A | 5/2008 |
| JP | 2008513763 A | 5/2008 |
| JP | 2008515557 A | 5/2008 |
| JP | 2008132342 A | 6/2008 |
| JP | 2008522642 A | 7/2008 |
| JP | 2008259541 A | 10/2008 |
| JP | 2008279274 A | 11/2008 |
| JP | 2008307087 A | 12/2008 |
| JP | 2009240667 A | 10/2009 |
| JP | 2010005375 A | 1/2010 |
| JP | 2010124842 A | 6/2010 |
| JP | 2010526626 A | 8/2010 |
| JP | 2011529362 A | 12/2011 |
| JP | 2013121493 A | 6/2013 |
| JP | 2014087448 A | 5/2014 |
| KR | 100715132 B | 4/2007 |
| KR | 1020080044737 A | 5/2008 |
| KR | 1020090103408 A | 10/2009 |
| WO | WO92/18054 A1 | 10/1992 |
| WO | WO98/00719 A2 | 1/1998 |
| WO | WO01/64109 A1 | 9/2001 |
| WO | WO02/084594 A2 | 10/2002 |
| WO | WO2005/009245 A1 | 2/2005 |
| WO | WO2006/114735 A1 | 11/2006 |
| WO | WO2007/127147 A2 | 11/2007 |
| WO | WO2008/097479 A1 | 8/2008 |
| WO | WO2009/060182 A2 | 5/2009 |
| WO | WO2010/095094 A1 | 8/2010 |
| WO | WO2010/137453 A1 | 12/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/112540 A2 | 8/2012 |
| WO | WO2012/131340 A2 | 10/2012 |
| WO | WO2012/160541 A2 | 11/2012 |
| WO | WO2013/059358 A2 | 4/2013 |
| WO | WO2013/109965 A1 | 7/2013 |
| WO | WO2013/116807 A1 | 8/2013 |
| WO | WO2013/116809 A1 | 8/2013 |
| WO | WO2013/116851 A1 | 8/2013 |
| WO | WO2013/116854 A1 | 8/2013 |
| WO | WO2013/116866 A1 | 8/2013 |
| WO | WO2013/128301 A2 | 9/2013 |

OTHER PUBLICATIONS

Arigovindan et al.; Full motion and flow field recovery from echo doppler data; IEEE Transactions on Medical Imaging; 26(1); pp. 31-45; Jan. 2007.

Cai et al.; Off-axis directional acoustic wave beaming control by an asymmetric rubber heterostructures film deposited on steel plate in water; IEEE Intl.; 2009 Ultrasonics Symposium (IUS); pp. 1552-1554; Rome; Sep. 2009.

Capineri et al.; A doppler system for dynamic vector velocity maps; Ultrasound in Medicine & Biology; 28(2); pp. 237-248; Feb. 28, 2002.

Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb 28, 2008.

Chen et al.; Maximum-likelihood source localization and unknown sensor location estimation for wideband signals in the near-field; IEEE Transactions on Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Cristianini et al.; An Introduction to Support Vector Machines; Cambridge University Press; pp. 93-111; Mar. 2000.

Dunmire et al.; A brief history of vector doppler; Medical Imaging 2001; International Society for Optics and Photonics; pp. 200-214; May 30, 2001.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 482, 484; Feb. 1994.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.

(56) References Cited

OTHER PUBLICATIONS

Hasegawa et al.; High frame rate ultrasonic imaging of the heart by placing virtual point sources in front of array; IEEE Intl.; 2013 Ultrasonics Symposium (IUS); pp. 581-584; Prague; Jul. 2013.
Haun et al.; Efficient three-dimensional imaging from a small cylindrical aperture; IEEE Trans. on Ultrasonics, Ferroelectrics, and Frequency Control; 49(7); pp. 861-870; Jul. 2002.
Haykin, Simon; Neural Networks: A Comprehensive Foundation (2nd Ed.); Prentice Hall; pp. 156-187; Jul. 16, 1998.
Heikkila et al.; A four-step camera calibration procedure with implicit image correction; Proceedings IEEE Computer Scociety Conference on Computer Vision and Pattern Recognition; San Juan; pp. 1106-1112; Jun. 17-19,1997.
Hendee et al.; Medical Imaging Physics; Wiley-Liss, Inc. 4th Edition; Chap. 19-22; pp. 303-353; (year of pub. sufficiently earlier than effective US filing date and any foreign priority date) © 2002.
Hsu et al.; Real-time freehand 3D ultrasound calibration; CUED/F-INFENG/TR 565; Department of Engineering, University of Cambridge, United Kingdom; 14 pages; Sep. 2006.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Kramb et al,.; Considerations for using phased array ultrasonics in a fully automated inspection system. Review of Quantitative Nondestructive Evaluation, 2004 Edition, ed. D. O. Thompson and D. E. Chimenti, American Inst. of Physics, pp. 817-825, Mar. 2004.
Ledesma-Carbayo et al.; Spatio-temporal nonrigid registration for ultrasound cardiac motion estimation; IEEE Trans. on Medical Imaging; vol. 24; No. 9; Sep. 2005.
Leotta et al.; Quantitative three-dimensional echocardiography by rapid imaging . . . ; J American Society of Echocardiography; vol. 10; No. 8; ppl 830-839; Oct. 1997.
Li et al.; An efficient speckle tracking algorithm for ultrasonic imaging; 24; pp. 215-228; Oct. 1, 2002.
Montaldo et al.; Building three-diminsional images using a time-reversal chaotic cavity; IEEE Trans. on Ultrasonics, Ferroelectrics, and Frequency Control; 52(9); pp. 1489-1497; Sep. 2005.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.
Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.
Saad et al.; Computer vision approach for ultrasound doppler angle estimation; Journal of Digital Imaging; 22(6); pp. 681-688; Dec. 1, 2009.
Sakas et al.; Preprocessing and volume rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; Jan. 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. on Neural Networks; vol. 2.; No. 6; Nov. 1991.
Specht, D.F.; Blind deconvolution of motion blur using LMS inverse filtering; Lockheed Independent Research (unpublished); Jun. 23, 1975.
Specht, D.F.; Enhancements to probabilistic neural networks; Proc. IEEE International Joint Conf. on Neural Networks; Baltimore, MD; Jun. 1992.
Specht, D.F.; GRNN with double clustering; Proc. IEEE International Joint Conf. Neural Networks; Vancouver, Canada; Jul. 16-21, 2006.
Specht, D.F.; Probabilistic neural networks; Pergamon Press; Neural Networks; vol. 3; pp. 109-118; Feb. 1990.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Urban et al; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs.); Jun. 2011.
Urban et al; Implementation of vibro-acoustography on a clinical ultrasound system; IEEE Ultrasonics Symposium (IUS); pp. 326-329; Oct. 14, 2010.
Von Ramm et al.; High-speed ultrasound volumetric imaging—System. 2. Parallel processing and image display; IEEE Trans. Ultrason., Ferroelect., Freq. Contr.; vol. 38; pp. 109-115; Mar. 1991.
Wang et al.; Photoacoustic tomography of biological tissues with high cross-section resolution: reconstruction and experiment; Medical Physics; 29(12); pp. 2799-2805; Dec. 2002.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Wikipedia; Point cloud; 2 pages; retrieved Nov. 24, 2014 from the internet (https://en.wikipedia.org/w/index.php?title=Point_cloud&oldid=472583138).
Wikipedia; Curve fitting; 5 pages; retrieved from the internet (http:en.wikipedia.org/wiki/Curve_fitting) Dec. 19, 2010.
Wikipedia; Speed of sound; 17 pages; retrieved from the internet (http:en.wikipedia.org/wiki/Speed_of_sound) Feb. 15, 2011.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Zhang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

* cited by examiner

ULTRASOUND IMAGING USING APPARENT POINT-SOURCE TRANSMIT TRANSDUCER

CROSS-REFERENCE TO RELATED APPLICATIONS

This application is a continuation of U.S. patent application Ser. No. 15/888,738, filed Feb. 5, 2018, which is a divisional of U.S. patent application Ser. No. 14/279,052, filed May 15, 2014, now U.S. Pat. No. 9,883,848, which application claims the benefit of U.S. Provisional Patent Application No. 61/877,555, filed Sep. 13, 2013, titled "Ultrasound Imaging Using Virtual Point-Source Transmission", herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates generally to the field of ultrasound imaging, and more particularly to ping-based ultrasound imaging using apparent point-source transmitters.

BACKGROUND

In conventional scanline-based ultrasonic imaging, a focused beam of ultrasound energy is transmitted into body tissues to be examined and echoes returned along the same line are detected and plotted to form a portion of an image along the scanline. A complete image may be formed by repeating the process and combining image portions along a series of scanlines within a scan plane. Any information in between successive scanlines must be estimated by interpolation.

The same process has been extended to obtaining ultrasonic images of three-dimensional volumes by combining images from multiple adjacent slices (where each slice is in a different scan plane). Again, any information from any space in between successive scan planes must be estimated by interpolation. Because time elapses between capturing complete 2D slices, obtaining 3D image data for a moving object may be significantly impaired. So-called "4D" imaging systems (in which the fourth dimension is time) strive to produce moving images (i.e., video) of 3D volumetric space. Scanline-based imaging systems also have an inherent frame-rate limitation which creates difficulties when attempting 4D imaging on a moving object.

As a result of these and other factors, some of the limitations of existing 2D and 3D ultrasonic imaging systems and methods include poor temporal and spatial resolution, imaging depth, speckle noise, poor lateral resolution, obscured tissues and other such problems.

Significant improvements have been made in the field of ultrasound imaging with the creation of multiple aperture imaging, examples of which are shown and described in Applicant's prior patents and applications referenced above. Multiple aperture imaging methods and systems allow for ultrasound signals to be both transmitted and received from physically and logically separate apertures.

SUMMARY OF THE DISCLOSURE

The various embodiments of systems and methods herein provide the ability to perform high resolution three-dimensional ultrasound imaging at frame rates sufficient to capture details of moving objects. Traditional scanline-based ultrasound imaging methods are limited to relatively slow frame rates due to the need to transmit and receive many scanlines to obtain a single two-dimensional plane. Extending such techniques to obtain imaging data from a complete 3D volume results in even slower frame rates due to the need to image many 2D slices.

As an example, assume that one needs to collect data from a cube of tissue 10 cm on a side at a depth ranging from 5 cm to 15 cm. If scanlines are transmitted from a common center, the shape that would be explored would be a truncated pyramid instead of a shape with comparable thickness in the proximal and distal regions. The tissue may be sampled with beams that are 2 mm (or less) apart on the distal face of the cube. To cover the distal surface one would need at least 50×50 directed beams or 2500 directed pulses. With a maximum pulse rate of approximately 2500 pulses/sec (which may be constrained by the speed of sound in tissue, the expected signal attenuation, and the background noise level), all of the required data may be collected in about one second. This collection time may be adequate for non-moving tissue such as bone, liver, etc., but is not fast enough to capture motion in arteries, or organs such as kidneys and especially the heart, or in moving joints or muscles.

On the other hand, with ping-based imaging, a single ping, propagating substantially uniformly in three dimensions, can insonify the entire volume, and dynamic beamforming (focusing) can identify the sources of the echo returns. Using ping-based imaging techniques, a minimum of three pings may be needed to obtain data for a 3D volume, while a minimum of two pings may be needed to obtain data for a 2D slice. In practical terms, ten to fifty (or more) pings may be used to achieve a desired image quality. For example, the use of 25 pings at a rate of 2500 pings per second may require only 0.01 seconds to acquire all the data for the entire 10 cm cube of tissue. For this particular example, data collection may be 100 times faster than with the scanline-based method.

Using ping-based ultrasound imaging techniques, both 2D and 3D frame rates may be increased substantially so as to allow for imaging of 3D volumes in real-time. Furthermore, by applying multiple aperture imaging techniques (e.g., transmitting and receiving ultrasound signals through multiple, spatially or physically separated acoustic windows), the resolution of such real-time 3D images may be dramatically improved relative to single-aperture techniques.

The following disclosure provides various embodiments of apparent point-source transducers, as well as systems and methods for using such apparent point-source transducers to perform high-frame-rate high-resolution real-time 2D, 3D and so-called 4D ultrasound imaging.

In one embodiment, a method of imaging an object with ultrasound energy is provided, the method comprising the steps of transmitting an un-focused ultrasound signal into a target medium from apparent point-source transmit transducer comprising a shell of piezoelectric material shaped as a spherical section with a spherical center point, receiving echoes reflected by a reflector in the target medium with an omnidirectional receive element that is different than the apparent point-source transmit transducer, determining a position of the reflector within the target medium by obtaining element position data describing a position of the spherical center point of the apparent point-source transmit transducer and a position of the receive element, calculating a total path distance as a sum of a first distance between the spherical center point and the reflector and a second distance between the reflector and the receive element, and determining a locus of possible points at which the reflector may lie, and producing an image of the reflector.

In some embodiments, the receive element comprises a shell of piezoelectric material shaped as a spherical section with a second spherical center point and wherein the position of the receive element is a position of the second spherical center point.

In another embodiment, the position of the receive element lies on a surface of the receive element.

In one embodiment, the method further comprises repeating the receiving, determining, and producing steps with a plurality of receive elements in a common receive aperture.

In one embodiment, the method further comprises repeating the receiving, determining, and producing with elements of a plurality of receive apertures.

In one embodiment, the method further comprises repeating the transmitting step with a separate second, apparent point-source transmit transducer.

In some embodiments, a straight-line distance between the apparent point-source transmit transducer and the receive element is greater than a maximum coherent aperture length for an intended imaging application.

In other embodiments, calculating the total path distance comprises adding apparent path segment representing a distance from a convex transmit transducer surface of the apparent point-source transmit transducer to the spherical center point.

In some embodiments calculating the total path distance comprises subtracting apparent path segment representing a distance from a concave transmit transducer surface of the apparent point-source transmit transducer to the spherical center point.

In alternative embodiments, the receive element has a circular shape.

An ultrasound imaging system is also provided, comprising a first apparent point-source transmit transducer shaped as a spherical section having a spherical center point, the first apparent point-source transmit transducer configured to transmit a three-dimensional semi-spherical pulse into a target object to be imaged, a first plurality of receive transducer elements configured to receive echoes of the three-dimensional semi-spherical pulse, a second plurality of receive transducer elements configured to receive echoes of the three-dimensional semi-spherical pulse, a controller configured to control transmission of the three-dimensional semi-spherical pulse and to determine a position of reflectors within the object based on a known position of the spherical center point of the apparent point-source transmit transducer, known positions of the elements of the first and second pluralities of receive transducer elements, a time at which the three-dimensional semi-spherical pulse was transmitted, and times at which the echoes are received.

In some embodiments, the first apparent point-source transmit transducer is convex relative to the target object.

In one embodiment, the first apparent point-source transmit transducer is concave relative to the target object.

In alternative embodiments, the first apparent point-source transmit transducer is shaped as a spherical section that is greater than half a sphere.

In some embodiments, the first apparent point-source transmit transducer is shaped as a spherical section that is less than half a sphere.

In one embodiment, the first apparent point-source transmit transducer is shaped as a spherical section that is half a sphere.

In some embodiments, the first apparent point-source transmit transducer has a spherical radius of between 0.2 mm and 10 mm.

In one embodiment, the first apparent point-source transmit transducer is configured to transmit ultrasound signals at a first frequency range.

In other embodiments, the first apparent point-source transmit transducer comprises a shell of piezoelectric material with a constant thickness.

In one embodiment, the system further comprises a second apparent point-source transmit transducer with a spherical radius and configured to transmit ultrasound signals at a second frequency range, the second frequency range being different than the first frequency range.

In some embodiments, the apparent point-source transmit transducer comprises a shell having a constant-thickness made of a continuous piezoelectric material.

In another embodiment, the apparent point-source transmit transducer comprises a shell having a constant-thickness made of a segmented piezoelectric material.

In some embodiments, the apparent point-source transmit transducer comprises a plurality of segments arranged into the spherical shape, wherein all segments are configured to transmit ultrasound signals simultaneously.

In one embodiment, the system further comprises a computer readable memory containing data describing a position of the spherical center point of the apparent point-source transmit transducer relative to at least one element of the first plurality of receive transducer elements.

In one embodiment, the system further comprises a computer readable memory containing an adjustment factor representing apparent path segment equal to a distance from a surface of the first apparent point-source transmit transducer to the spherical center point.

In another embodiment, each of the first plurality of receive elements and the second plurality of receive elements has a circular shape.

An ultrasound probe comprising: an apparent point-source transmit transducer comprising a shell of piezoelectric material shaped as a spherical section with a constant wall thickness and a spherical center point; and a receive array comprising a plurality of omnidirectional receive transducer elements, the receive array having a total aperture greater than a coherence width for an intended imaging application.

In some embodiments, the plurality of receive transducer elements are grouped into separate arrays.

In another embodiment, the plurality of receive transducer elements are contained in a continuous array.

In some embodiments, the receive elements have a cylindrical shape.

In additional embodiments, the receive elements have a spherical section shape.

In alternative embodiments, the ultrasound probe is sized and configured for insertion into a body lumen or cavity.

In one embodiment, the ultrasound probe is sized to cover approximately half of a human patient's chest.

In some embodiments, the total aperture is at least twice a coherence width for the intended imaging application.

In other embodiments, the total aperture is at least three times a coherence width for the intended imaging application.

In one embodiment, the probe comprises an array of transducer elements with a width of about 8 cm to about 10 cm.

An apparent point-source ultrasound transducer element is provided, comprising a shell of piezoelectric material shaped as a spherical section with a constant wall thickness and a spherical center point, a convex surface, and a concave surface, an acoustic damping material surrounding and bonded to the convex surface of the shell, and an electrical lead extending through the acoustic damping material and connected to the convex surface of the shell.

In one embodiment, the element further comprises an acoustic matching material filling and bonded to the concave surface of the shell.

In some embodiments, the shell has a transmitting surface shaped as a spherical section that is greater than half a sphere.

In other embodiments, the shell has a transmitting surface shaped as a spherical section that is less than half a sphere.

In additional embodiments, the shell has a transmitting surface shaped as a spherical section that is half a sphere.

In some embodiments, the shell is made of a composite material comprising a piezoelectric ceramic and a polymer.

In other embodiments, the shell comprises lead zirconate titanate (PZT).

In one embodiment, the shell has a transmitting surface area of at least three square millimeters.

In another embodiment, the shell has a transmitting surface area of at least five square millimeters.

In one embodiment, the shell has a transmitting surface area of at least ten square millimeters.

An apparent point-source ultrasound transducer element is also provided, comprising a shell of piezoelectric material shaped as a spherical section with a constant wall thickness and a spherical center point, a convex surface and a concave surface, an acoustic damping material filling and bonded to the concave surface of the shell, and an electrical lead extending through the acoustic damping material and connected to the concave surface of the shell.

In one embodiment, the element further comprises an acoustic matching material bonded to the convex surface of the shell.

In some embodiments, the shell has a transmitting surface shaped as a spherical section that is greater than half a sphere.

In another embodiment, the shell has a transmitting surface shaped as a spherical section that is less than half a sphere.

In one embodiment, the shell has a transmitting surface shaped as a spherical section that is half a sphere.

In an alternative embodiment, the shell is made of a composite material comprising a piezoelectric ceramic and a polymer.

In some embodiments, the shell comprises lead zirconate titanate (PZT).

In other embodiments, the shell has a transmitting surface area of at least three square millimeters.

In one embodiment, the shell has a transmitting surface area of at least five square millimeters.

In another embodiment, the shell has a transmitting surface area of at least ten square millimeters.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
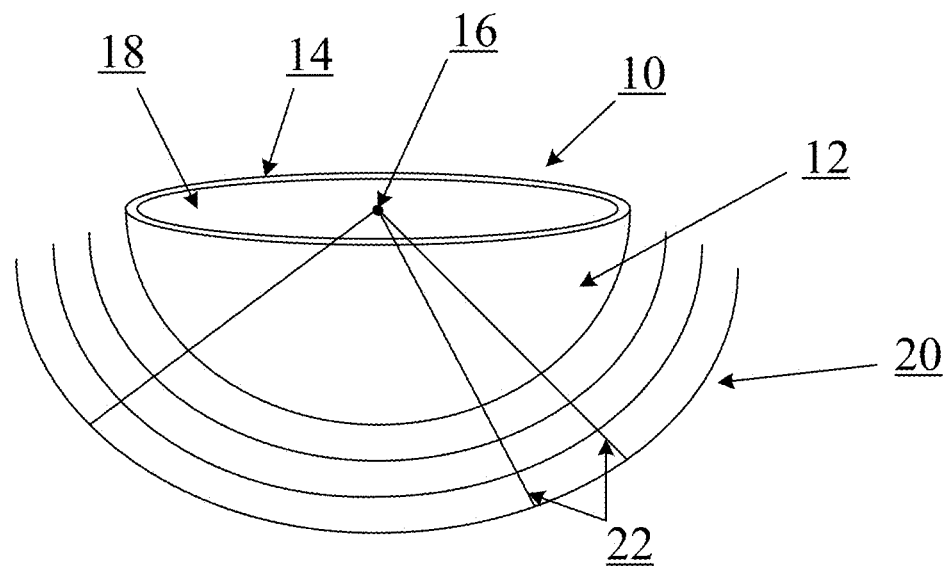
FIG. 1 is a perspective view of one embodiment of a convex apparent point-source transmit transducer element.

The various embodiments will be described in detail with reference to the accompanying drawings. References made to particular examples and implementations are for illustrative purposes, and are not intended to limit the scope of the invention or the claims.

The present disclosure provides systems and methods for improving the quality of 2D, 3D and 4D ultrasound images through the use of one or more apparent point-source ultrasound transmitters. In some embodiments, such apparent point-source transmitters may be used in combination or integrally with multiple aperture ultrasound imaging systems, multiple aperture ultrasound probes, and/or multiple aperture ultrasound beamforming techniques. Various embodiments of such systems, methods and combinations are provided herein.

Although the various embodiments are described herein with reference to ultrasound imaging of various anatomic structures, it will be understood that many of the methods and devices shown and described herein may also be used in other applications, such as imaging and evaluating non-anatomic structures and objects. For example, the various embodiments herein may be applied to non-destructive testing applications such as evaluating the quality, integrity, dimensions, or other characteristics of various structures such as welds, pressure vessels, pipes, structural members, beams, etc. The systems and methods may also be used for imaging and/or testing a range of materials including human or animal tissues, solid metals such as iron, steel, aluminum, or titanium, various alloys or composite materials, etc.

Introduction to Key Terms

The following paragraphs provide useful definitions for some terms used frequently herein. Other terms may also be defined as they are used below.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In other embodiments, ultrasound transducers may comprise capacitive micro-machined ultrasound transducers (CMUT) or any other transducing device capable of converting ultrasound waves to and from electrical signals.

Transducers are often configured in arrays of multiple individual transducer elements. As used herein, the terms "transducer array" or "array" generally refers to a collection of transducer elements mounted to a common backing plate. Such arrays may have one dimension (1D), two dimensions (2D), 1.X dimensions (1.XD) or three dimensions (3D) as those terms are used elsewhere herein and/or as they are commonly understood in the art. Other dimensioned arrays as understood by those skilled in the art may also be used. Annular arrays, such as concentric circular arrays and elliptical arrays may also be used. An element of a transducer array may be the smallest discretely functional component of an array. For example, in the case of an array of piezoelectric transducer elements, each element may be a single piezoelectric crystal or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound signal. Transmitted ultrasound signals may be focused in a particular direction, or may be unfocused, transmitting in all directions or a wide range of directions. Similarly, the term "receive element" may refer without limitation to an ultrasound transducer element which at least momentarily performs a receive function in which an ultrasound signal impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" may refer to a conceptual "opening" through which ultrasound signals may be sent and/or received. In actual practice, an aperture is simply a single transducer element or a group of transducer elements that are collectively managed as a common group by imaging control electronics. For example, in some embodiments an aperture may be a grouping of elements which may be physically separate and distinct from elements of an adjacent aperture. However, adjacent apertures need not necessarily be physically separate or distinct. Conversely, a single aperture may include elements of two or more physically separate or distinct transducer arrays. For example, distinct groups of transducer elements (e.g., a "left aperture") may be constructed from a left array, plus the left half of a physically distinct center array, while a "right aperture" may be constructed from a right array, plus the right half of a physically distinct center array).

It should be noted that the terms "receive aperture," "insonifying aperture," and/or "transmit aperture" are used herein to mean an individual element, a group of elements within an array, or even entire arrays, that perform the desired transmit or receive function from a desired physical viewpoint or aperture. In some embodiments, such transmit and receive apertures may be created as physically separate components with dedicated functionality. In other embodiments, any number of send and/or receive apertures may be dynamically defined electronically as needed. In other embodiments, a multiple aperture ultrasound imaging system may use a combination of dedicated-function and dynamic-function apertures.

As used herein, the term "total aperture" refers to the overall size of all imaging apertures in a probe. In other words, the term "total aperture" may refer to one or more dimensions defined by a maximum distance between the furthest-most transducer elements of any combination of send and/or receive elements used for a particular imaging cycle. Thus, the total aperture may be made up of any number of sub-apertures designated as send or receive apertures for a particular cycle. In the case of a single-aperture imaging arrangement, the total aperture, sub-aperture, transmit aperture, and receive aperture may all have the same dimensions. In the case of a multiple aperture imaging arrangement, the dimensions of the total aperture includes the sum of the dimensions of all send and receive apertures plus any space between apertures.

In some embodiments, two apertures may be located adjacent to one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

Elements and arrays described herein may also be multi-function. That is, the designation of transducer elements or arrays as transmitters in one instance does not preclude their immediate re-designation as receivers in the next instance. Moreover, embodiments of the control system herein include the capabilities for making such designations electronically based on user inputs, pre-set scan or resolution criteria, or other automatically determined criteria.

Introduction to Point-Source Transmission Ultrasound Imaging

In various embodiments, point-source transmission ultrasound imaging, otherwise referred to as ping-based ultrasound imaging, provides several advantages over traditional scanline-based imaging. Point-source transmission differs in its spatial characteristics from a "phased array transmission" which focuses energy in a particular direction from the transducer element array along a directed scanline. A point-source pulse (ping) may be transmitted so as to generate either a two-dimensional a circular wavefront or a three-dimensional spherical wavefront in the scanning plane, thereby insonifying as wide an area as possible. Echoes from scatterers in the region of interest may return to all of the elements of receive apertures. Those echo signals may be filtered, amplified, digitized and stored in short term or long term memory (depending on the needs or capabilities of a particular system).

Images may then be reconstructed from received echoes by assuming that the wavefronts emitted from the point-source are physically circular in the region of interest. In actuality, the wavefront may also have some penetration in the dimension orthogonal to the scanning plane (i.e., some energy may essentially "leak" into the dimension perpendicular to the desired two-dimensional scanning plane, reducing the effective imaging depth). Additionally, the "circular" wavefront may actually be limited to a semicircle or a fraction of a circle less than 180 degrees ahead of the front face of the transducer according to the unique off-axis properties of the transducing material used. Similarly, a "spherical" wavefront may have an actual shape of a hemisphere or less than a hemisphere within the medium to be imaged.

A software-based, firmware-based, or hardware-based dynamic beamforming technique, in which a beamformer's focus may be continuously changed to focus at a particular pixel position as that pixel is being imaged, may be used to plot the position of echoes received from a point-source pulse. In some embodiments, a dynamic beamformer may plot the locus of each echo signal based on a round-trip travel time of the signal from the transmitter to an individual receive transducer element.

The locus of a single reflector will lie along either a two-dimensional ellipse (in the case of two-dimensional imaging) or a three-dimensional ellipsoid (in the case of three-dimensional imaging). A first focus of the ellipse or ellipsoid will be at the position of the transmit transducer element and the second focus will be at the position of the receive transducer element. Although several other possible reflectors lie along the same ellipse or ellipsoid, echoes of the same reflector will also be received by each of the other receive transducer elements of a receive aperture. The slightly different positions of each receive transducer element means that each receive element will define a slightly different ellipse or ellipsoid for a given reflector. Accumulating the results by coherently summing the ellipses or ellipsoids for all elements of a common receive aperture will indicate an intersection of the ellipses or ellipsoids for a reflector, thereby converging towards a point at which to display or define a pixel or voxel representing the reflector. The echo amplitudes received by any number of receive elements may thereby be combined into each pixel or voxel value. In other embodiments the computation can be organized differently to arrive at substantially the same image.

Various algorithms may be used for combining echo signals received by separate receive elements. For example, some embodiments may process echo-signals individually, plotting each echo signal at all possible locations along its ellipse, then proceeding to the next echo signal. Alternatively, each pixel location may be processed individually, identifying and processing all echoes potentially contributing to that pixel location before proceeding to the next pixel location.

Image quality may be further improved by combining images formed by the beamformer from one or more subsequent transmitted pings, transmitted from the same or a different point-source (or multiple different point-sources). Still further improvements to image quality may be obtained by combining images formed by more than one receive aperture. An important consideration is whether the summation of images from different pings, different transmit point-sources or different receive apertures should be coherent summation (phase sensitive) or incoherent summation (summing magnitude of the signals without phase information).

The decision as to whether to use coherent or incoherent summation may be influenced by the lateral extent/size of the receive aperture(s) and/or the transmit aperture(s). In some embodiments, it may be convenient to confine the size of an aperture to conform to the assumption that the average speed of sound is substantially the same for every path from a scatterer to each element of the receive aperture. For narrow receive apertures this simplifying assumption is easily met. However, as the width of the receive aperture increases, an inflection point is reached (referred to herein as the "maximum coherent aperture width" or "maximum coherence width"), beyond which the paths traveled by returning echoes of a common reflector will necessarily pass though different types of tissue having intrinsically different speeds of sound. When this difference results in receive wavefront phase shifts approaching or exceeding 180 degrees, additional receive elements extended beyond the maximum coherence width will actually degrade the image rather than improve it. The same considerations may also apply to the size of transmit apertures, which may include a plurality of coherently combined transducer elements. In the case of two-dimensional transducer arrays used in three-dimensional imaging (or 3D data collection), it may be useful to define a maximum coherent aperture size in two dimensions. Thus, in various embodiments a maximum coherent aperture may be defined as a group of transducer elements in a square, circle, polygon or other two-dimensional shape with a maximum distance between any two elements such that phase cancellation will be avoided when echo data received at the elements of the aperture are coherently combined.

Therefore, in order to realize the inherent benefits (e.g., in terms of increased spatial resolution) of a wide probe with a total aperture width far greater than the maximum coherent aperture width, the full probe width may be physically or logically divided into multiple apertures, each of which may be limited to an effective width less than or equal to the maximum coherent aperture width, and thus small enough to avoid phase cancellation of received signals. The maximum coherence width can be different for different patients (or different test objects) and for different probe positions on the same patient. In some embodiments, a compromise width may be determined for a given probe system. In other embodiments, a multiple aperture ultrasound imaging control system may be configured with a dynamic algorithm to subdivide the available elements in multiple apertures into groups that are small enough to avoid significant image-degrading phase cancellation. In various embodiments, a particular coherent aperture size may be determined automatically by a control system, or manually through user input via a user control such as a dial or slider.

In some embodiments, coherent (phase sensitive) summation may be used to combine echo data received by transducer elements located on a common receive aperture resulting from one or more pings. In some embodiments, incoherent summation may be used to combine echo data or image data received by separate receive apertures if such receive apertures that could possibly contain phase-cancelling data. Such may be the case with receive apertures that have a combined total aperture that is greater than a maximum coherence width for a given imaging target.

Point-Source Transmission for 3D Ultrasound Imaging

When a three-dimensional pulse is initiated from a point-source transmit transducer, the resulting semi-spherical wavefront travels into the region of interest (ROI) where some of the ultrasound energy may be reflected by scatterers in the ROI. Some of the echoes from the scatterers may travel back towards receive transducer elements of the probe, where the echoes may be detected, amplified, digitized, and stored in a short-term or long-term memory device. Each digitized sample value may represent a scatterer from the ROI. As in the 2D case, the magnitude of each received sample, along with its time of arrival and the exact positions of the transmit and receive transducers used, may be analyzed to define a locus of points identifying potential positions of the scatterer. In the 3D case, such a locus is an ellipsoid having as its foci the positions of the transmit and receive transducers. Each unique combination of transmit and receive transducer elements may define a separate view of the same reflector. Thus, by combining information from multiple transmit-receive transducer combinations, the actual location of each reflector may be more accurately represented.

For example, in some embodiments an image in a 3D array of voxels may be assembled in computer memory by beginning with an evaluation of a selected digital sample. The selected digitized sample value may be written into every voxel indicated by the corresponding ellipsoid described above. Proceeding to do the same with every other collected sample value, and then combining all resulting ellipsoids may produce a more refined image. Real scatterers would be indicated by the intersection of many ellipsoids whereas parts of the ellipsoids not reinforced by other ellipsoids would have low levels of signal and may be treated as noise (i.e., eliminated or reduced by filters or other image processing steps).

In other embodiments, the order of computation may be changed by beginning with a selected voxel in a final 3D image volume to be produced. For example, for a selected voxel, the closest stored sample may be identified for each transmitter/receiver pair. All samples corresponding to the selected voxel may then be evaluated and summed (or averaged) to produce a final representation of the voxel. Closeness of a sample to a selected voxel may be determined by calculating the vector distance from the three-dimensional position of a transmitter (i.e., the transmitter used to produce the sample) to the selected voxel position plus the vector distance from the selected voxel position to the position of a receiver used to produce the sample. Such a linear distance may be related to the time-divided sample values by dividing the total path length by speed of sound through the imaged object. Using such a method, the samples corresponding to a calculated time may be associated with the selected voxel.

Techniques for determining the location for received echo samples are generally referred to herein as beamforming, while techniques for combining information obtained from multiple transmitter/receiver combinations or from multiple separate pings transmitted using the same transmitter/receiver combination may generally be referred to as image layer combining. In various embodiments, a frame may be made up of any number of combined image layers. Frames may be displayed sequentially at a desired frame-rate on a display to form a moving image or video. The above-described beamforming processes may beneficially also be used for evaluating pixel values in a 2D cross-sectional slice through a 3D volume using raw echo data. In various embodiments, such 2D slices may be taken at any arbitrary angle or along any curved path through the 3D volume. The same techniques may also be used to zoom in (i.e., increase the size of features) using raw echo data rather than enlarging processed pixels or voxels.

Apparent Point-Source Transmitters

As described above, a point-source transmitter may be approximated using a single small transducer element of a transducer array. When performing 2D ping imaging using a 1D array (an array of elements with parallel longitudinal axes, typically including a lens to focus the signal into a single imaging plane), a single element may be able to produce a ping with sufficient energy in the imaging plane to achieve imaging at a reasonable depth. However, when imaging is purposefully extended into the third dimension, a single small transmit element of a typical transducer array may be insufficient to produce a ping with enough energy to obtain a viable image at the desired depth due to insufficient signal power. This may be understood in view of the fact that the power of a transmitted ultrasound pulse is dispersed in three dimensions rather than two, so the log amplitude of the wavefront attenuates according to an inverse-square relation rather than linearly. Depending on the frequency of the transmitted pulse and the attenuation rate of the material under observation, a low energy ping may weaken beneath the background noise level before returning a usable signal at desired depth. One solution may be to transmit a "ping" from multiple adjacent elements, but the more elements used, the less the transmit aperture approximates a point-source, which may have the effect of distorting the semi-spherical shape of the transmitted waveform (or semi-circular shape in the 2D case), which may result in reduced image quality. Using multiple transmit elements also reduces precision in the determination of a point to use as the transmit-source ellipsoid focus during beamforming calculations, thereby further reducing image quality. Such reduced image quality may be acceptable in some applications, but in other applications a higher quality image may be desired.

In various embodiments, an "apparent point-source transmitter" transducer may be configured to produce a waveform that both approximates an actual point-source and has sufficient energy to produce high quality images at the desired depth. In some cases, such apparent point-source transmitters may be configured such that ultrasound power output may be limited only by safety considerations within the imaged medium.

As used herein, the phrase "point-source" refers to a point in 3D space that represents a center point of a transmitted 2D or 3D ultrasound waveform. In some embodiments, such a point is ideally an infinitely small point corresponding to a produced wavefront with a consistent semi-spherical shape. In embodiments in which such a waveform is produced by a single small element, such a point may lie on the surface of the transducer element. As used herein, the terms "semi-spherical pulse" and "semi-spherical wavefront" may refer to any ultrasound wavefront with a spherical-section shape, including wavefronts with approximately spherical-section shapes greater than or less-than an ideal semi-sphere. Similarly, the terms "semi-circular pulse" and "semi-circular wavefront" may refer to any ultrasound wavefront which appears in an imaging plane to have a circular-section shape, including wavefronts with approximately circular-section shapes greater than or less-than an ideal semi-circle.

In some cases, multiple (e.g., two, three, four or more) small transducer elements from a common transmit/receive array may be excited simultaneously to produce a ping with more energy than may be produced by a single element. As a practical matter, when using multiple small elements to approximate a point-source transmitter, the "point" may effectively be larger and more spread out, which may tend to cause a loss of precision in beamforming calculations using the center "point" as the location of the transmitted ping (and, by extension, as one of the foci—along with the location of the receive element—of the ellipsoid representing the locus of all points for any given time-of-travel). Such a spread out or "smeared" transmit point may also lead to potentially undesirable variation in the shape of the produced waveform from an ideal semi-sphere. Some variation may be inevitably present in any point-source transmitter, but better results may be achieved with a point-source transmitter that produces a waveform as close to the ideal as possible.

An alternate solution is to provide a large transducer shaped and configured to produce a relatively high-power waveform that "appears" to have originated from a point-source—in other words, apparent point-source. When performing beamforming calculations to determine the location of reflectors based on the timing of received echoes, the location of the apparent point-source may be used as the origin of the transmitted ping wavefront. In some embodiments, particularly suitable shapes for transmitting transducers may include concave and convex spherical caps. Convex spherical caps may generally be referred to herein as "dome-shaped," while concave spherical caps may be referred to as "bowl-shaped." Some examples of imaging probes incorporating examples of such transducer elements are provided below.

An apparent point-source may exist when the point defining the origin of the semi-spherical wavefront lies somewhere other than on the surface of the transducer producing the wavefront. If the medium is assumed to be below or in front of the transducer, apparent point-source located above or behind a transducer surface may be referred to herein as a "negative" apparent point-source. On the other hand, apparent point-source located below the transducer surface may be referred to herein as a "positive" apparent point-source. A transducer configured to produce a wavefront that appears to have originated from apparent point-source may be referred to herein as an "apparent point-source transducer."

FIG. 1 illustrates an embodiment of apparent point-source transmit transducer 10 comprising a relatively large dome-shaped ultrasound transducer (e.g., having a spherical radius 15 greater than the wavelength of ultrasound in the target medium) with a three-dimensional convex transducing surface 12 relative to the imaged medium. A convex dome-shaped transducer 10 may be used to produce a negative apparent point-source transmitter at a point above or within the transducer in order to produce a wavefront of a desired shape downward into an object to be imaged. An example propagating ping waveform 20 produced by a dome-shaped transducer 10 is also shown in FIG. 1. As indicated by ray lines 22, the wavefront 20 has the same shape as if it were emitted from the point 16 at the spherical center of the transducer 10.

An apparent point-source transducer 10 may comprise a shell 14 of a material exhibiting piezoelectric properties. The shell 14 may have a substantially constant thickness throughout. The transducer 10 may further include one or more electrical conductors extending from an interior surface 18 of the transducer shell 14. In the case of a dome-shaped transducer, the concave volume within the shell 14 may be filled with an acoustic damping material. Examples of suitable acoustic damping materials include polyurethanes, acrylics, epoxies (e.g., doped epoxies, such as tungsten-doped epoxy) or any other suitable acoustic backing materials.

In theory, a transducer in the shape of a complete sphere may produce a perfectly spherical wavefront with an apparent origin at the center of the sphere. However, the need for mechanical and electrical control of a transducer in a practical imaging system necessitates truncating the sphere to some degree. Thus, in some embodiments, a convex dome-shaped apparent point-source transducer 10 such as that shown FIG. 1 may have the shape of a sphere truncated to form a spherical cap.

Figure 2A:
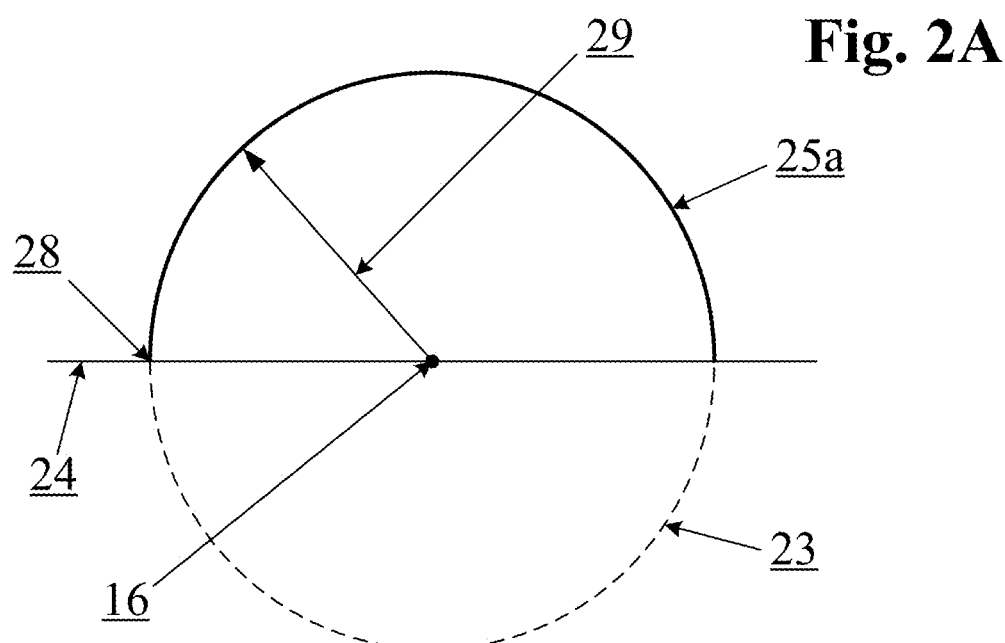
FIG. 2A is a two-dimensional (2D) cross-sectional illustration of a semi-spherical transducer shape.
Figure 2B:
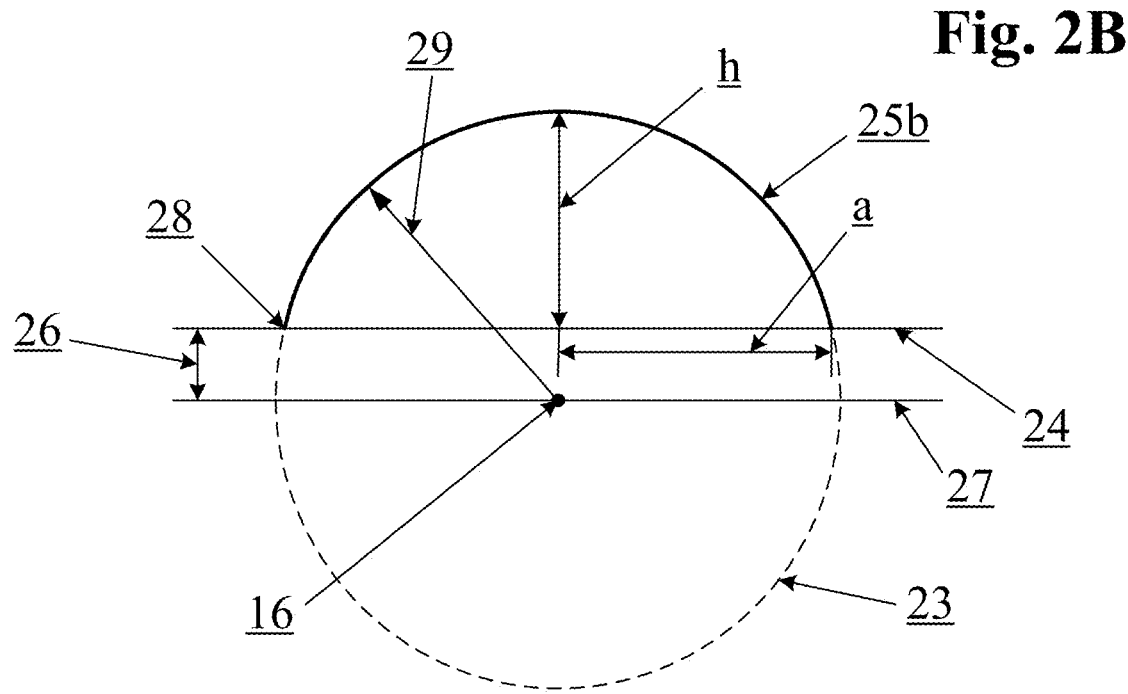
FIG. 2B is a two-dimensional cross-sectional illustration of a transducer shaped as a spherical cap that is less than half a sphere.
Figure 2C:
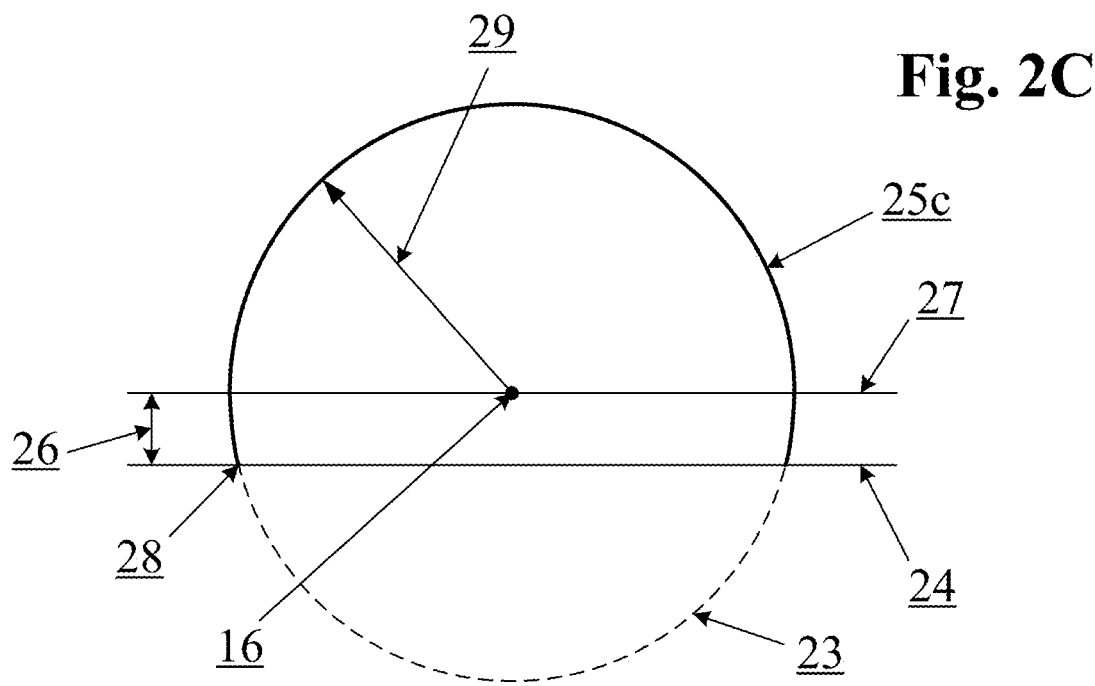
FIG. 2C is a two-dimensional cross-sectional illustration of a transducer shaped as a spherical cap that is greater than half a sphere.

The diagrams of FIG. 2A, FIG. 2B and FIG. 2C illustrate a cross-sectional view of a complete sphere 23 from which a spherical cap 25 may be truncated by a truncation plane 24. The truncation plane 24 may pass through, above or below the spherical center point 16. In some embodiments, the truncation plane 24 may intersect the spherical center point 16, resulting in a spherical cap 25a that is exactly half a sphere as shown in FIG. 2A. In alternative embodiments, the truncation plane 24 may pass through the sphere 23 at a point above the spherical center 16 resulting in a spherical cap 25b that is less than half of a sphere as shown in FIG. 2B. In other embodiments, the truncation plane 24 may pass through the sphere 23 at a point below the spherical center 16, resulting in a spherical cap 25c greater than half a sphere as shown in FIG. 2C.

The intersection 28 of the truncation plane 24 and the sphere 23 will be referred to herein as a cut circle which has a cut radius that is mathematically related to the spherical radius according to the equation:

$$a = \text{sqrt}(R^2 - E^2)$$

Where a is the cut radius, R is the spherical radius and E is the cut elevation. R-E is the height (h) of the spherical cap.

The surface area of the resulting spherical cap is also mathematically related to the spherical radius (R) and the cut elevation (E) according to the equation:

$$A_{cap} = 2 * \pi * R * (R - E)$$

The spherical radius used in the above equations should be the radius to the intended active transducer surface. Thus, for a convex dome-shaped transducer made from a transducer shell with a thickness t, the transducer surface area may be calculated using the outer spherical radius, which is equal to the inner radius plus the thickness.

The perpendicular distance 26 between the truncation plane 24 and a parallel plane 27 through the spherical center 16 will be referred to herein as the cut elevation. Cut elevation may be expressed as an actual distance or as a percent of the spherical radius 29. A cut elevation of exactly zero corresponds to a perfectly semi-spherical cap, while a cut elevation of 99% would result in a very small cap section with a surface area of about 0.5% of a complete sphere. As used herein, a positive cut elevation refers to a spherical cap such as that shown in FIG. 2B in which the resulting spherical cap is less than half a sphere, and a negative cut elevation refers to a spherical cap such as that shown in FIG. 2C in which the resulting spherical cap is more than half a sphere.

Figure 3A:
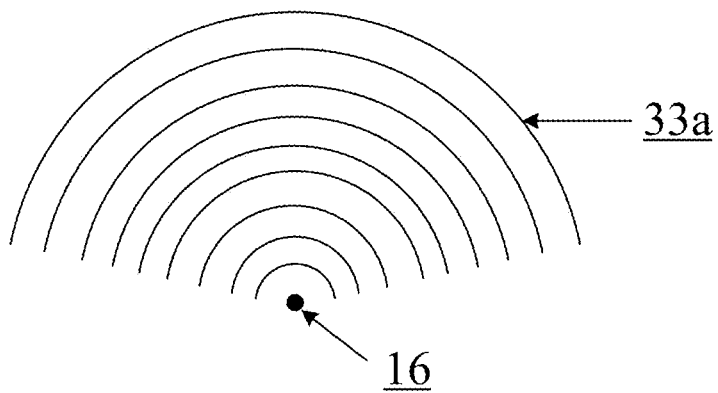
FIG. 3A is a two-dimensional cross-sectional illustration of a three-dimensional (3D) waveform produced by apparent point-source ultrasound transducer with a cut elevation of zero and therefore a perfectly semi-spherical convex transducer surface.
Figure 3B:
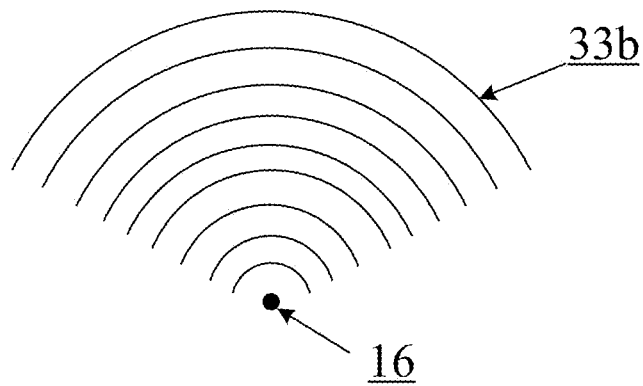
FIG. 3B is a two-dimensional cross-sectional illustration of a three-dimensional waveform produced by apparent point-source ultrasound transducer with a cut elevation of 60% of the spherical radius and therefore a convex transducer surface in the shape of less than half a sphere.
Figure 3C:
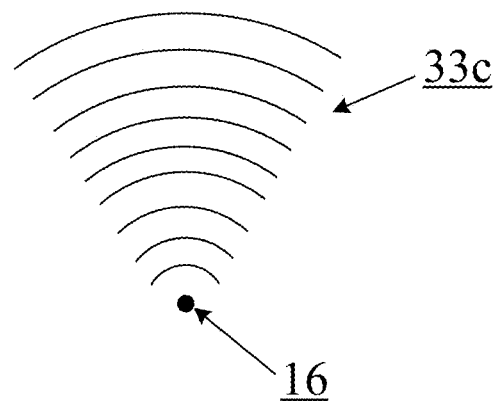
FIG. 3C is a two-dimensional cross-sectional illustration of a three-dimensional waveform produced by apparent point-source ultrasound transducer with a cut elevation of 98% of the spherical radius and therefore a convex transducer surface in the shape of a very small section of a sphere.

FIGS. 3A-3D illustrate two-dimensional cross-sectional views of 3D waveforms 33a-33d that may be produced by apparent point-source transducers with a range of cut elevations. FIG. 3A represents a simulated 3D waveform 33a resulting from apparent point-source transducer with a cut elevation of zero, meaning that the convex transducer has a surface of about half a sphere (i.e., about 50% of a complete sphere) and a cut radius equal to the spherical radius. As shown, the portion of the resulting waveform 33a with power above a desired threshold may be slightly less than perfectly semi-spherical due to edge-effects of the dome-shaped transducer. FIG. 3B represents a simulated 3D waveform 33b resulting from apparent point-source transducer with a cut elevation of about 60% of the spherical radius, meaning that it has a convex transducer surface of about 20% of a complete sphere and a cut radius of about 80% of the spherical radius. FIG. 3C represents a simulated 3D waveform 33c resulting from apparent point-source transducer with a cut elevation of about 98% of the spherical radius, meaning that it has a convex transducer surface of about 1% of a complete sphere and a cut radius of approximately 20% of the spherical radius.

Figure 3D:
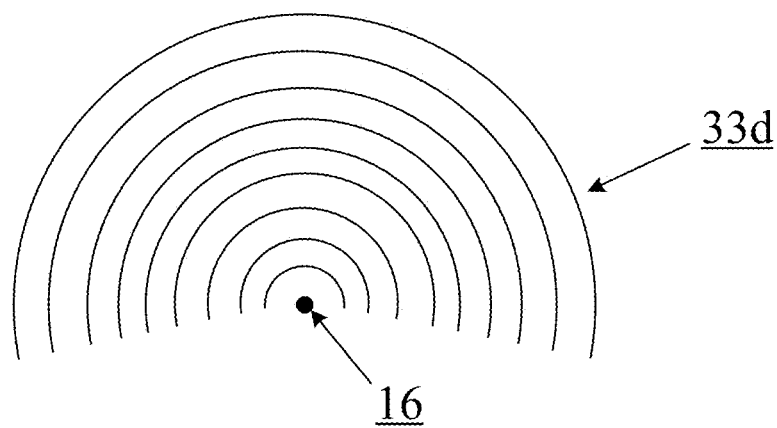
FIG. 3D is a two-dimensional cross-sectional illustration of a three-dimensional waveform produced by apparent point-source ultrasound transducer with a cut elevation of −60% of the spherical radius and therefore a convex transducer surface in the shape of a more than half a sphere.

FIG. 3D represents a 3D waveform 33d that may result from apparent point-source transducer with a slightly negative cut elevation. For example, the waveform 33d may result from apparent point-source transducer with a cut elevation of −20% of the spherical radius, meaning that it has a convex transducer surface of about 60% of a complete sphere and a cut radius of about 98% of the spherical radius. Although the examples of FIGS. 3A-3D are based on convex apparent point-source transducers, similar results may be achieved with apparent point-source transducers with concave spherical cap shapes.

In any event, when performing ping-based, non-focused ultrasound imaging using an ultrasound transducer having the shape of a spherical cap, the spherical center point 16 may be treated as the mathematical origin of a wavefront emitted by the transducer for purposes of triangulation. The same may also be applied to convex (bowl-shaped) transducers.

Figure 4:
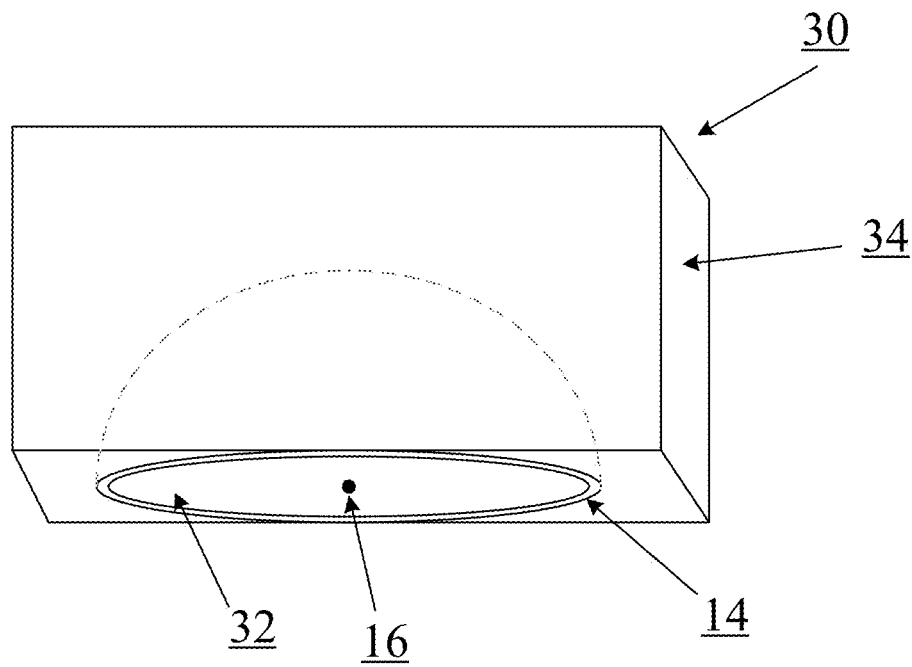
FIG. 4 is a perspective view of one embodiment of a concave apparent point-source transmit transducer element.

FIG. 4 illustrates an embodiment of a bowl-shaped apparent point-source transducer 30 including a shell 14 of piezoelectric material and an acoustic backing material 34 surrounding the convex side of the shell 14. As with the dome-shaped transducers described above, the apparent point-source of an ultrasound wavefront produced by a bowl-shaped transducer will be the spherical center 16. In the case of a bowl-shaped transducer, it may be desirable to construct the shell 14 as a spherical cap that is no more than half of a sphere. Thus, in some embodiments, a bowl-shaped transducer 30 may have a concave surface 32 that is less than half a sphere. The spherical center of such a shape, and therefore the apparent point-source, may be located below the extent of the transducer.

In cases where living human or animal tissue is to be imaged, it may be desirable to keep the apparent point-source of a bowl transducer (i.e., the spherical center point at which ultrasound waves converge) from occurring too near or inside the living tissue. In some embodiments, this may be achieved by selecting appropriate spherical cap dimensions and/or by assembling probes with bowl-shaped apparent point-source transducers with one or more matching layers or other materials with a thickness sufficient to include the spherical center point. Thus, in some embodiments, a concave region of a bowl-shaped apparent point-source transducer 30 may be filled with an acoustic-coupling material that may be selected to have an inherent speed-of-sound substantially matching the medium to be imaged. The coupling material, which may also be referred to as a matching layer, may comprise any suitable material, such as saline solutions, glycerine, propylene glycol, silicone (e.g., RTV silicone), ballistic gelatin or other matching layer or lensing layer materials known to be suitable for use in ultrasound imaging of humans or animals. Alternatively, materials such as acrylics, glass, metals, composites, etc. may be used in matching layers for NDT (Non-Destructive Test) imaging of mechanical, structural or other non-living objects. In some embodiments, such a matching material may extend beyond the ring edge of the transducer shell 14 sufficiently to include the spherical center point 16, thereby eliminating any potential risk that may be presented by ultrasound energy converging at that point within an imaged medium.

In some embodiments, a larger apparent point-source transducer may be capable of inducing a higher energy wavefront in an imaged medium. In general, the maximum energy or power that may be produced by apparent point-source transducer may be proportional to the surface area of the transducer. The actual power produced by a transducer in a particular application may be controlled by varying the magnitude, frequency, duration, duty cycle, or other characteristics of an applied voltage signal. As a result, larger apparent point-source transducers may be used to transmit 3D ultrasound pings with more energy than smaller apparent point-source transducers.

The exact size of apparent point-source transducer may be partially dependent on the application in which it is to be used. Ultrasound signals attenuate as they pass through materials being imaged. As a result, the transmitted signal must have enough power that it may travel into the medium, reflect off of structures to be imaged, and return to the receive transducers with sufficient power that the signal may be adequately distinguished from noise. Thus, on one hand, it is desirable to provide the capability of transmitting ultrasound signals with as much power as possible. On the other hand, practical factors may limit the power level that may be safely used before causing injury (e.g., to human or animal patients being imaged) or damage (e.g., to sensitive materials or equipment being imaged or tested).

Because a desired maximum transducer power may be proportional to the transducer's surface area, the spherical radius and/or the cut elevation of apparent point-source transmit transducer may be selected based on a desired transducer surface area. For example, a 1D transducer element with a length of 14 mm and a width of 0.25 mm has a surface area of 3.5 mm$^2$. If it is desired to make an equivalent apparent point-source transmitter, the same surface area may be achieved with an embodiment of a spherical cap apparent point-source transducer having a cut elevation of zero and a spherical radius of about 0.75 mm. In another embodiment, the same 3.5 mm$^2$ surface area may also be achieved with a spherical cap apparent point-source transducer having a spherical radius of about 0.8 mm and a cut elevation of about 10% of the spherical radius (i.e., a cap height of about 0.7 mm and a cut radius of about 0.78 mm).

In various embodiments, any of various attributes such as the transducer surface area, the cut radius, the spherical radius, cap height, cut elevation, etc. may be used as a design starting point. In some cases, a particular surface area may be desired so as to achieve a desired transmit power level. Various examples of apparent point-source geometries based on various surface areas are provided in Table 1 below.

TABLE 1

Spherical Cap Geometries for Apparent Point-Source Ultrasound Transmitters

| Cut Elevation (%) | Cap Area | Sphere Radius | Cap Height | Cut Radius | Cap as % of Sphere |
|---|---|---|---|---|---|
| −30% | 3 mm$^2$ | 0.61 mm | 0.79 mm | 0.58 mm | 65% |
| −10% | 3 mm$^2$ | 0.66 mm | 0.72 mm | 0.66 mm | 55% |
| 0% | 3 mm$^2$ | 0.69 mm | 0.69 mm | 0.69 mm | 50% |
| 10% | 3 mm$^2$ | 0.73 mm | 0.66 mm | 0.72 mm | 45% |
| 30% | 3 mm$^2$ | 0.83 mm | 0.58 mm | 0.79 mm | 35% |
| −30% | 10 mm$^2$ | 1.11 mm | 1.44 mm | 1.06 mm | 65% |
| −10% | 10 mm$^2$ | 1.20 mm | 1.32 mm | 1.20 mm | 55% |
| 0% | 10 mm$^2$ | 1.26 mm | 1.26 mm | 1.26 mm | 50% |
| 10% | 10 mm$^2$ | 1.33 mm | 1.20 mm | 1.32 mm | 45% |
| 30% | 10 mm$^2$ | 1.51 mm | 1.06 mm | 1.44 mm | 35% |
| −30% | 30 mm$^2$ | 1.92 mm | 2.49 mm | 1.83 mm | 65% |
| −10% | 30 mm$^2$ | 2.08 mm | 2.29 mm | 2.07 mm | 55% |
| 0% | 30 mm$^2$ | 2.19 mm | 2.19 mm | 2.19 mm | 50% |
| 10% | 30 mm$^2$ | 2.30 mm | 2.07 mm | 2.29 mm | 45% |
| 30% | 30 mm$^2$ | 2.61 mm | 1.83 mm | 2.49 mm | 35% |
| −30% | 60 mm$^2$ | 2.71 mm | 3.52 mm | 2.59 mm | 65% |
| −10% | 60 mm$^2$ | 2.95 mm | 3.24 mm | 2.93 mm | 55% |
| 0% | 60 mm$^2$ | 3.09 mm | 3.09 mm | 3.09 mm | 50% |
| 10% | 60 mm$^2$ | 3.26 mm | 2.93 mm | 3.24 mm | 45% |
| 30% | 60 mm$^2$ | 3.69 mm | 2.59 mm | 3.52 mm | 35% |

Alternatively, factors such as probe geometry or intended imaging target may be more easily met by designing apparent point-source transmitters based on spherical radius, cap height, cut radius or other geometric factors.

TABLE 2

Spherical Cap Geometries for Apparent Point-Source Ultrasound Transmitters

| Cut Elevation (%) | Cap Area | Sphere Radius | Cap Height | Cut Radius | Cap as % of Sphere |
|---|---|---|---|---|---|
| −30% | 8.2 mm$^2$ | 1.0 mm | 1.30 mm | 0.95 mm | 65% |
| −10% | 6.9 mm$^2$ | 1.0 mm | 1.10 mm | 0.99 mm | 55% |
| 0% | 6.3 mm$^2$ | 1.0 mm | 1.00 mm | 1.00 mm | 50% |
| 10% | 5.7 mm$^2$ | 1.0 mm | 0.90 mm | 0.99 mm | 45% |
| 30% | 4.4 mm$^2$ | 1.0 mm | 0.70 mm | 0.95 mm | 35% |
| −30% | 32.7 mm$^2$ | 2.0 mm | 2.60 mm | 1.91 mm | 65% |
| −10% | 27.6 mm$^2$ | 2.0 mm | 2.20 mm | 1.99 mm | 55% |
| 0% | 25.1 mm$^2$ | 2.0 mm | 2.00 mm | 2.00 mm | 50% |
| 10% | 22.6 mm$^2$ | 2.0 mm | 1.80 mm | 1.99 mm | 45% |
| 30% | 17.6 mm$^2$ | 2.0 mm | 1.40 mm | 1.91 mm | 35% |
| −30% | 73.5 mm$^2$ | 3.0 mm | 3.90 mm | 2.86 mm | 65% |
| −10% | 62.2 mm$^2$ | 3.0 mm | 3.30 mm | 2.98 mm | 55% |
| 0% | 56.5 mm$^2$ | 3.0 mm | 3.00 mm | 3.00 mm | 50% |
| 10% | 50.9 mm$^2$ | 3.0 mm | 2.70 mm | 2.98 mm | 45% |
| 30% | 39.6 mm$^2$ | 3.0 mm | 2.10 mm | 2.86 mm | 35% |

In other embodiments, apparent point-source transducers of different sizes may be used for imaging at different depths. In some cases, larger transducers may also be more susceptible to manufacturing variation. Such variation may lead to transducers that create non-uniform wavefronts. In some embodiments, the degree to which transducer surface irregularities may negatively affect imaging performance may be a function of the ultrasound wavelength being used. For example, higher frequency ultrasound (often best suited for relatively shallow-depth imaging due to typically greater attenuation as a function of imaging depth) may require a more accurate spherical surface than lower frequencies which may be better suited to deeper imaging. The term "near field" may generally refer to a region of the image plane nearest to the transducer. Thus, in some embodiments, relatively larger transducers may be used for imaging mid-field and/or far-field regions of a patient or object, while relatively smaller transducers may be used for imaging near-field regions.

For example, a smaller spherical cap apparent point-source transducer with a spherical radius of up to about 0.75 mm may be well suited to imaging near-field regions, and may be configured to transmit at relatively high frequencies (e.g., between about 5 MHz and about 10 MHz or more) for imaging at relatively shallow depths (e.g., to about 5-10 cm in human tissue). In other embodiments, a relatively larger apparent point-source transducer (e.g., with a spherical radius between about 0.75 mm and about 6 mm) may be well suited to imaging somewhat deeper regions, and may be operated to transmit at relatively low frequencies (e.g., between about 1 MHz and about 5 MHz) for imaging relatively deeper regions (e.g., greater than 10 cm).

Thus, in various embodiments, apparent point-source probes for use with ping-based multiple aperture ultrasound imaging techniques may contain one or more spherical cap apparent point-source transducers with a spherical radius of between about 0.2 mm and about 10 mm or more.

In some embodiments, one or more apparent point-source transmit transducers within an ultrasound probe may be operated at different power levels and/or at different frequencies when operating in different imaging modes in order to optimally image at a wide range of depths. In some embodiments, such imaging modes may be manually selected by an operator of an imaging system, and in other embodiments, such modes may be automatically selected based on a pre-programmed imaging process for a chosen imaging scenario.

Examples of Piezoelectric Materials and Manufacturing

As described above, a dome-shaped or bowl-shaped transducer may be in the form of a thin shell of a piezoelectric material in the shape of a truncated spherical cap. Such a shell may be made of any material exhibiting piezoelectric properties. Many naturally occurring and synthetic materials are known to exhibit piezoelectric properties that may be of a character suitable for use in ultrasound imaging applications. In the case of ping-based multiple aperture ultrasound imaging, ultrasound ping signals may be transmitted at frequencies commonly used in diagnostic medical ultrasound, e.g., in the range of about 1 MHz to about 20 MHz or more. Thus, apparent point-source transducers with fundamental frequencies within this range may be suitable for use in ping-based multiple aperture imaging.

Naturally-occurring piezoelectric materials include quartz, topaz and tourmaline, while man-made piezoelectric ceramic materials include lead zirconate titanate (PZT), barium titanate, lead metaniobate, & polyvinylidene difluoride ($PVF_2$—not naturally piezoelectric, but may be made so by heating in the presence of a strong electrical field). Some man-made piezoelectric ceramic materials may be combined with non-piezoelectric polymer materials to create piezo-composites.

The thickness of apparent point-source transducer shell (whether bowl-shaped or dome-shaped) may be directly related to the fundamental frequency of the transducer. In some cases (e.g., for some piezoelectric ceramic materials), the thickness of a transducer shell may be equal to about half a wavelength of its corresponding fundamental frequency, or an odd number of wavelength halves such as 3/2 wavelength or 5/2 wavelength. However, depending on the materials used, the shell thickness may be differently related to the transducer's fundamental frequency. Manufacturing processes may also vary depending on the piezoelectric material used and other factors.

In order to produce a spherical-section shell with a substantially constant thickness, if there is a requirement that the shell have a thickness of half a wavelength, then there may be a minimum size for apparent point-source transducer configured for a particular fundamental frequency. For example, apparent point-source transducer sized for a fundamental frequency of 3 MHz may have a shell thickness of approximately ¼ mm (assuming a speed-of-sound of about 1550 m/s) and may have a minimum external diameter of about 1 mm. In other cases, smaller external diameters may be possible by using a different material, designing for a different speed-of-sound application, etc.

In some cases, the speed-of-sound characteristics of the piezoelectric material of the transducer itself may have directional characteristics (e.g., sound may travel faster along one crystal axis than another). In such cases, the shape of apparent point-source transducer may be varied from an ideal physical sphere (and/or by varying the transducer material thickness in portions of the sphere) in order to create a transducer that produces a more uniform spherical-section wavefront in the material to be imaged.

Figure 5:
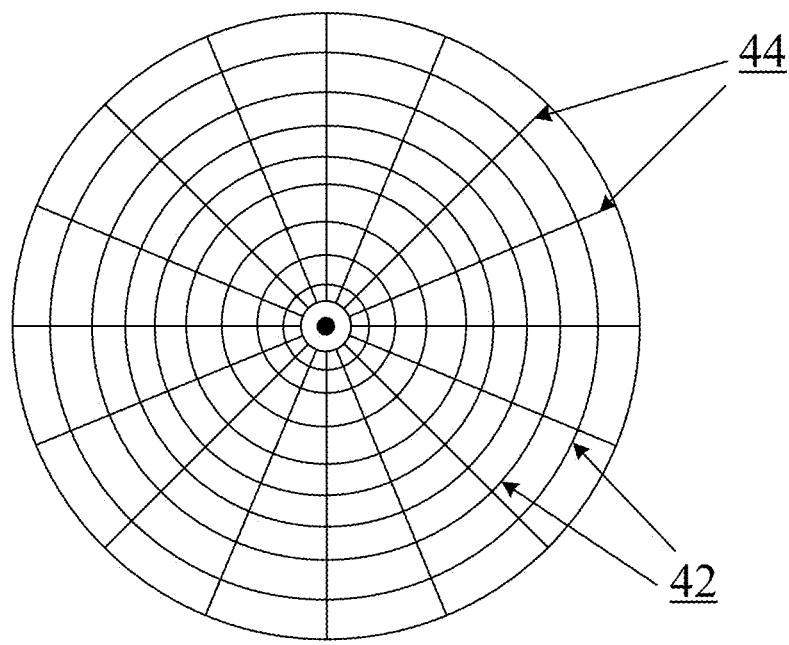
FIG. 5 is a plan view illustrating an embodiment of cut lines in a planar sheet of piezoelectric material to be formed into a spherical cap.

For example, natural or man-made piezoelectric material may be machined using traditional techniques in order to form the desired shape directly from a block of material. Such machining may be performed using mechanical cutters, water jets or any other available machining technique. Alternatively, a block or sheet of piezoelectric material may be machined into a plurality of elements attached to a flexible substrate which may then be formed into the desired shape. For example, a plurality of concentric ring cuts 42 and radial cuts 44 may be made in a sheet of piezoelectric material (as shown for example in FIG. 5), which may then be formed over a backing material with the desired spherical-cap shape. In such embodiments, the individual elements may be electrically connected so as to transmit simultaneously without phasing.

In some embodiments, a desired shape may be molded (e.g., by injection molding, die casting, or other molding process) from a piezo-composite material. Examples of molding processes that may be adapted to forming spherical-cap elements are described in U.S. Pat. Nos. 5,340,510 and 5,625,149.

It is also possible to produce ultrasound transducers in a desired shape using additive manufacturing techniques (commonly known as 3D printing techniques). For example, US Patent Publication 2013/0076207 and US Patent Publication 2013/0088122 describe systems and methods for forming transducers in the shape of cylindrical posts. Similar techniques may also be adapted to form transducers with spherical-cap shapes. Additionally, other manufacturing techniques such as laser sintering, stereo lithography, chemical vapor deposition or any other suitable techniques may be used to produce transducers in the shapes and sizes described herein.

Capacitive Micromachined Ultrasound Transducer (CMUT) formation techniques may also be used to form transducers of desired shapes onto a pre-shaped substrate. WO 2012/112540 shows and describes some examples of structures and techniques that may be adapted to forming spherical-cap shaped transducers. Alternately, a dome-shaped transducer may be made by forming an array of CMUT transducers on a substrate pre-formed into a desired shape (e.g., a concave or convex spherical cap as described above). In such embodiments, the CMUT elements may be electrically connected so as to transmit simultaneously without phasing.

Multiple Aperture Probes with Apparent Point-Source Transmitters

Apparent point-source transmitter transducers may be integrated into multiple aperture ultrasound probes designed for 2D or 3D imaging. Ultrasound probes configured for 3D ping-based multiple aperture imaging may comprise transducers arranged in an array extending substantial lengths in at least two dimensions across the surface of the object to be imaged. In some embodiments, some 3D probes may be used for apparent 2D imaging by only displaying a 2D slice while capturing data for a complete 3D volume, as described in further detail below.

Figure 6:
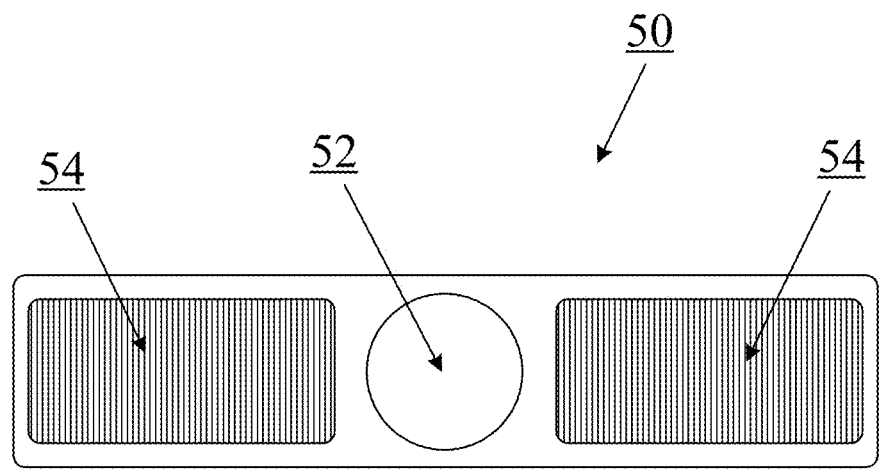
FIG. 6 is a face view of an embodiment of an ultrasound probe head configured for performing two-dimensional ping-based multiple aperture imaging and including apparent point-source transmit transducer.

FIG. 6 illustrates a probe 60 configured for 3D ping-based multiple aperture ultrasound imaging using apparent point-source transmitter 62. The probe 60 may comprise one or more apparent point-source transmitter transducers 62 and a plurality of transducer arrays 64. In various embodiments, the transducer arrays may be 2D or other matrix arrays of transducer elements. As described in further detail below, the receive elements may be provided in a range of sizes and shapes (e.g., square, circular or other polygonal elements, apparent point spherical cap elements, cylindrical elements, etc.).

Figure 7:
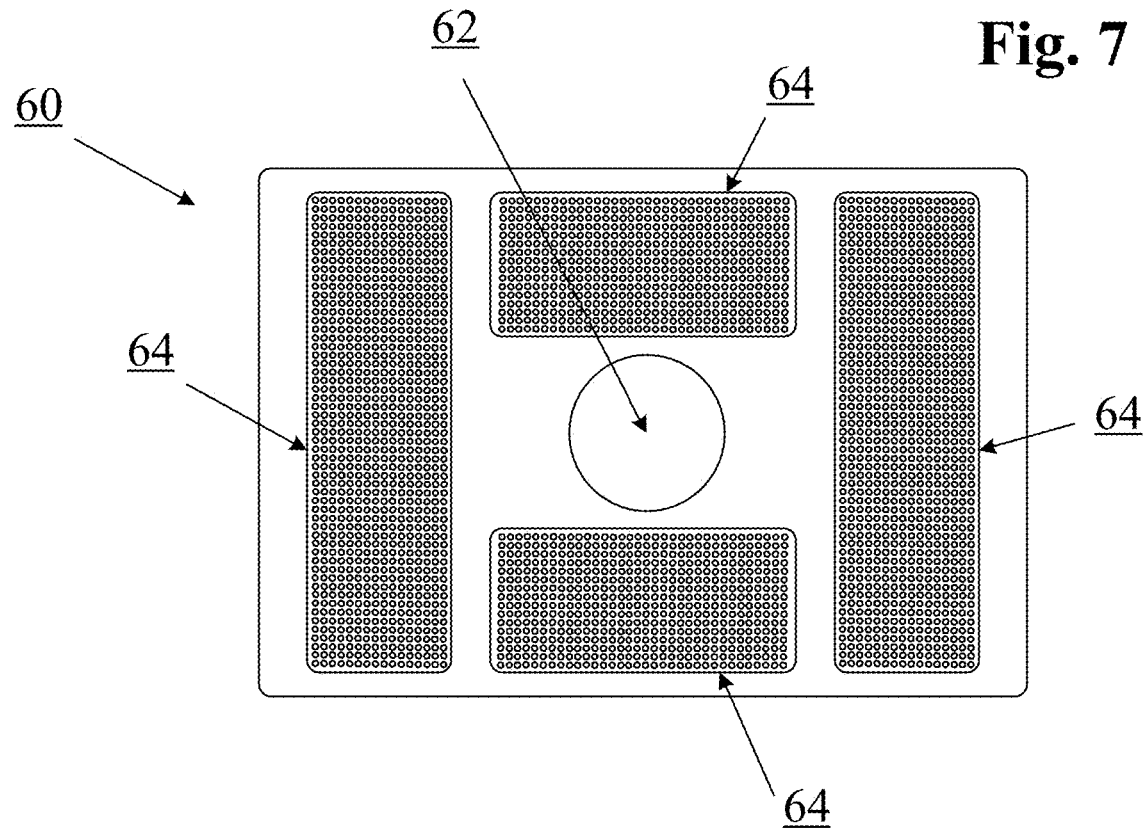
FIG. 7 is a face view of an embodiment of an ultrasound probe head configured for performing three-dimensional ping-based multiple aperture imaging and including apparent point-source transmit transducer.

FIG. 7 illustrates an alternative embodiment of a probe 61 configured for 3D ping-based multiple aperture imaging using at least two apparent point-source transmitters 62. The apparent point-source transducers 62 may be surrounded by a plurality of transducer arrays 64 of transducer elements.

The transducer arrays may be 2D or other matrix arrays made up of elements of any suitable shape as further described below.

Figure 8:
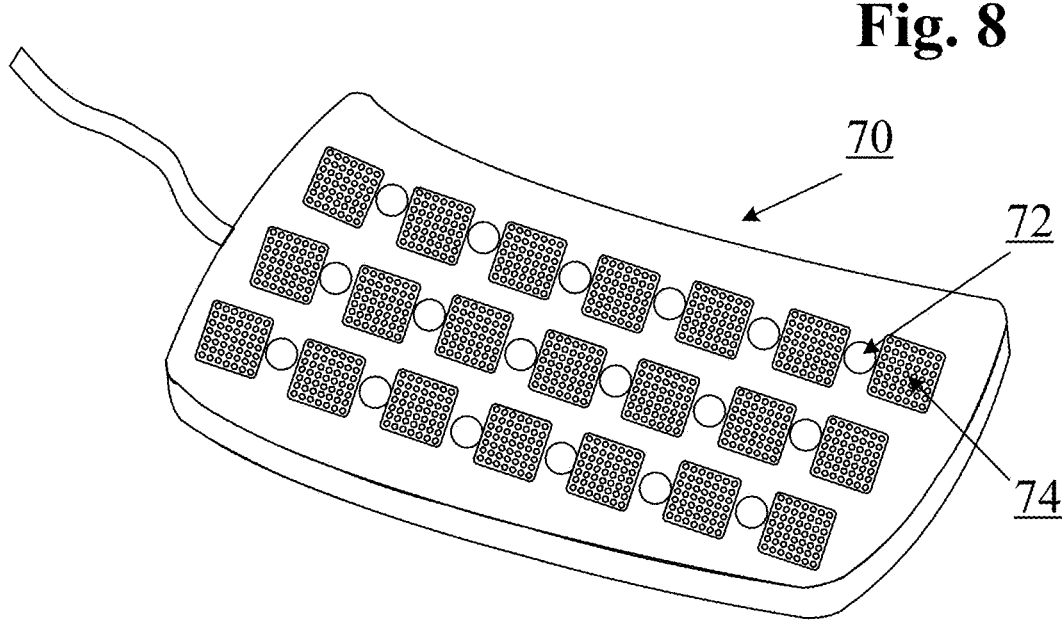
FIG. 8 is a perspective view of an embodiment of an ultrasound probe configured for performing 3D ping-based multiple aperture imaging and including a plurality of apparent point-source transmit transducers and a plurality of receiver arrays.

FIG. 8 illustrates an embodiment of a 3D ping-based multiple aperture ultrasound probe 70 comprising a plurality of apparent point-source transmitter transducers 72 and a plurality of transducer arrays 74 that may be used for receiving and/or transmitting ultrasound signals as will be further described below. The transducer arrays may be 2D or other matrix arrays. The probe configuration of FIG. 8 provides the benefits of a large probe incorporating multiple apparent point-source transmitters while making use of commodity 2D (or other) transducer arrays for receiving and additional imaging functions (e.g., transmitting phased array pulses, Doppler pulses, etc.).

In some embodiments, the probe 70 of FIG. 8 may have a rectangular, square, elliptical, circular or other shape with an overall size of up to about 10 cm (4") or more. As described elsewhere herein, ping-based multiple aperture imaging techniques may make use of such a large total aperture to form high-resolution ultrasound images.

As in the example of FIG. 8, the transducer arrays 74 may be arranged parallel to one another. In alternative embodiments, some arrays may be arranged with long axes perpendicular to one another or at other angles relative to one another. Probes may also include any number of apparent point-source transmitters and rectangular arrays in any geometric arrangement as needed for a particular application.

Figure 9:
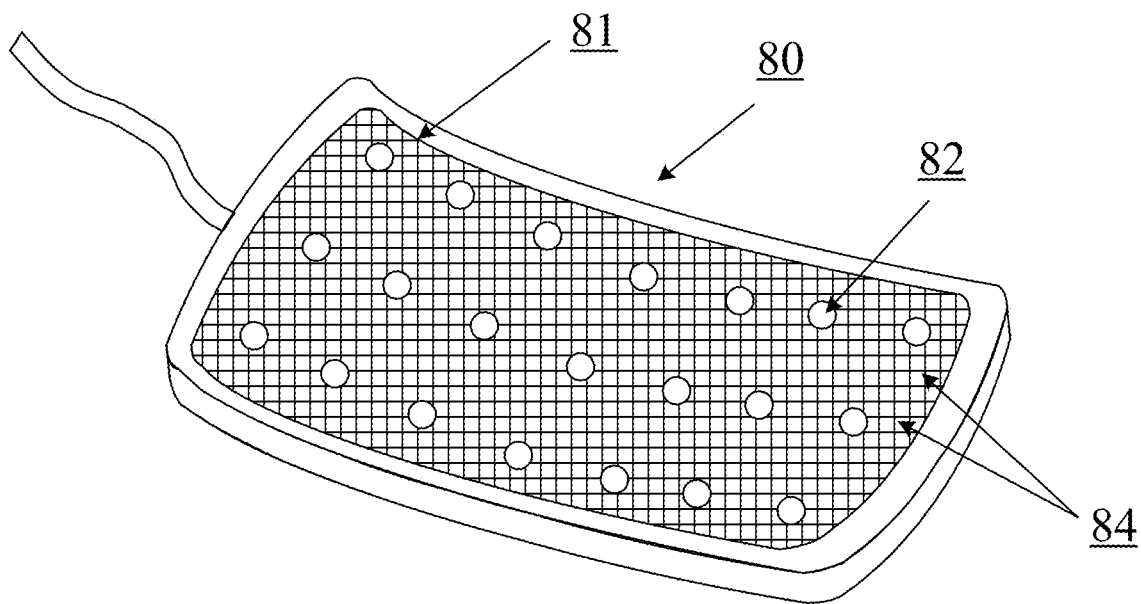
FIG. 9 is a perspective view of an embodiment of an ultrasound probe configured for performing 3D ping-based multiple aperture imaging and including a continuous array of transducer elements with a plurality of integrated apparent point-source transmit transducers.

FIG. 9 illustrates another embodiment of a 3D ping-based multiple aperture ultrasound probe 80 comprising a large continuous transducer array 81 that includes a plurality of apparent point-source transmitter transducers 82 and a plurality of small receive elements 84. In some embodiments, the large transducer array 81 may be substantially planar. Alternatively, the large transducer array 81 may be concave in one or two dimensions relative to an object to be imaged. A one-dimensional concave array may take the shape of an arc, while a two-dimensional concave array may be shaped more like a bowl or dish. In further embodiments, the array 81 may include both planar and concave sections. The small receive transducer elements 84 may be the size of any typical 2D array elements (e.g., between about 0.01 mm and about 0.5 mm square, circular or polygonal shaped elements). In still other embodiments, a continuous probe with a plurality of apparent point-source transducers such as the examples shown in FIG. 8 and FIG. 9 may also be provided with a convex surface for contacting an object to be imaged.

In various embodiments, transducer elements configured for receiving echoes of three-dimensional pings transmitted from apparent point-source transducer (e.g., receive elements 84) may themselves have spherical-section shapes defining apparent point receive elements. Receive transducer elements with spherical-section shapes may be well-suited to receiving echoes from all directions (i.e., omnidirectionally, or from as many directions as possible based on other constraints) from within a three-dimensional volume of the imaged medium. In some embodiments, apparent point-source transducer probe may comprise an array of apparent point-source transducers, each of which may comprise an independent concave or convex spherical-section shell. Such an array of apparent point-source transducer elements may include some elements that may be substantially larger than other elements. Alternatively, an array of apparent point-source transducer elements may be substantially the same size as one another. When receive elements are small, other shapes may also provide sufficient omnidirectionality for uniformly receiving echoes from a complete volume.

Other receive-element shapes may also be used, depending on the size of such receive elements, and trade-offs such as that between probe manufacturability and image quality. Thus, in some embodiments transducer elements configured for receiving echoes of three-dimensional pings transmitted from apparent point-source transducer may alternatively have substantially circular receiving surfaces that may be planar, convex or concave. In elevation, such elements may have cylindrical or otherwise shaped sides. In further embodiments, transducer elements configured for receiving echoes of three-dimensional pings transmitted from apparent point-source transducer may have planar, concave or convex receiving surfaces with other shapes such as polygonal (e.g., square, hexagonal, octagonal, etc.).

Therefore, some probes may include a combination of transducers with different shapes and sizes in a variety of configurations. For example, in some embodiments, apparent point receive transducer elements may be arranged in arrays made up of aligned rows and columns, offset rows and/or columns, radial lines, rings, random arrays, or any other configuration. Apparent point receive elements may generally be substantially smaller than apparent point-source transmitters in the same probe, while retaining substantially omnidirectional receiving ability.

In various embodiments, a probe configured for 2D or 3D ping-based multiple aperture imaging may include multiple sizes of apparent point-source transmit transducers. As described above, larger apparent point-source transmit transducers may be beneficial for deep-tissue imaging, while smaller apparent point-source transmit transducers may be beneficial for relatively shallower-tissue imaging. In some embodiments, a probe may include apparent point-source transmit transducers of various sizes, each size being optimized for imaging at a particular depth. In some embodiments, images obtained at various depths may be combined to form a continuous image extending from relatively shallow regions to relatively deep regions.

Figure 10:
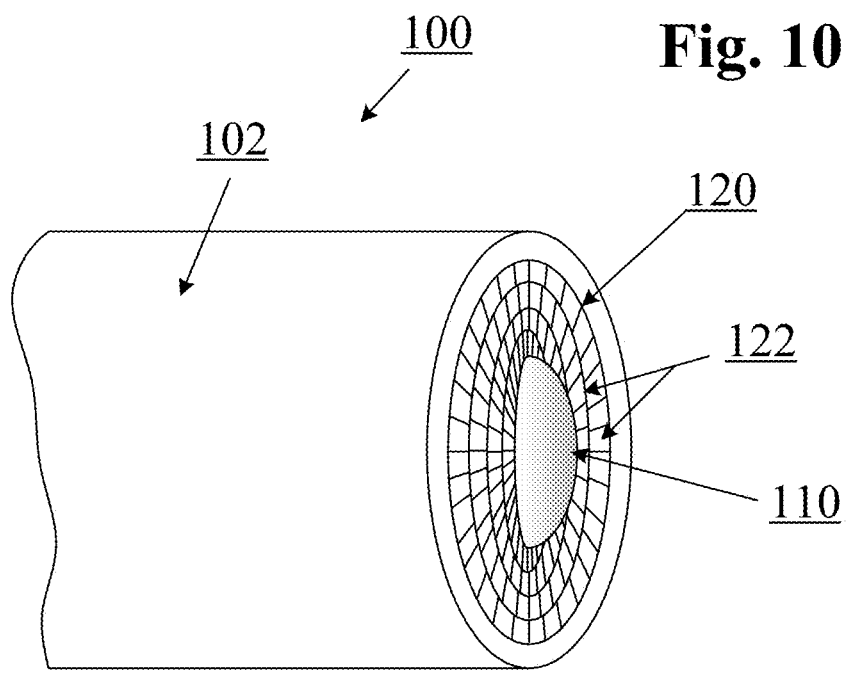
FIG. 10 is a perspective illustration of an embodiment of an intravenous ultrasound imaging probe carrying apparent point-source transmit transducer and a receive array.

In other embodiments, apparent point-source transducers may be used in combination with ultrasound probes sized to be inserted into a blood vessel or other bodily lumen within a patient (e.g., trans-esophageal probes, trans-urethral, trans-rectal probes, trans-vaginal probes). FIG. 10 illustrates an embodiment of an intra-vascular ultrasound probe 100 comprising a steer-able catheter body 102 carrying apparent point-source transducer 110 surrounded by an array 120 of receive elements 122. In some embodiments, the receive array 120 may lie on a single plane that is substantially perpendicular to a longitudinal axis of the catheter body 102.

Figure 10A:
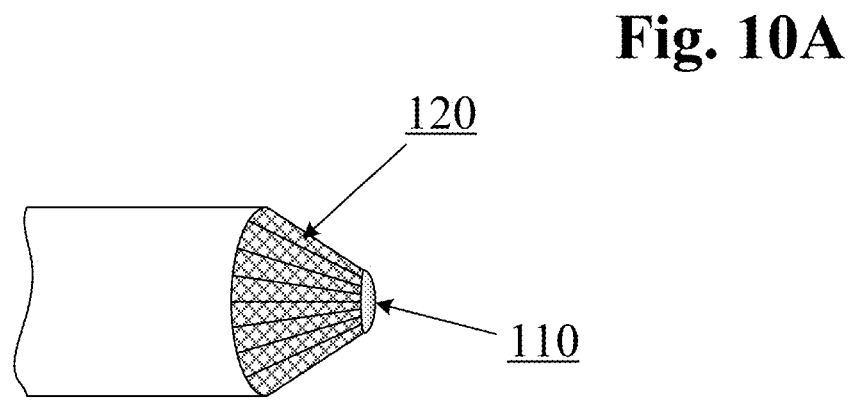
FIG. 10A is a cross-sectional view of an alternative embodiment of an intravenous ultrasound imaging probe carrying apparent point-source transmit transducer and a receive array.

Alternatively, as shown in FIG. 10A, the receive array 120 may be in the shape of a cone-shaped surface joined to the apparent point-source transmitter 110 which may be concentrically or eccentrically arranged relative to the cone. In still other embodiments, the receive array 120 may lie on a cylindrical surface with an axis parallel to the longitudinal axis of the catheter body 102. Alternatively, the receive array 120 may lie on any other concave or convex curved surface.

In some embodiments, apparent point-source transmit transducer may be provided on a separate probe from a receive transducer. Separate probes may have separate cables and may be entirely independent of one another. In other cases, a mechanical linkage may join the transmit and receive probes. When there is no mechanical linkage between separate transmit and receive transducers, the location of the transmit transducer can be determined by triangulation using receive timing from multiple receivers in the receive probe. Once the location of the transmitting apparent point-source is determined, the location of each of the scatterers in the tissue can be determined as described above using the intersection of ellipsoids generated via multiple receive elements.

Figure 10B:
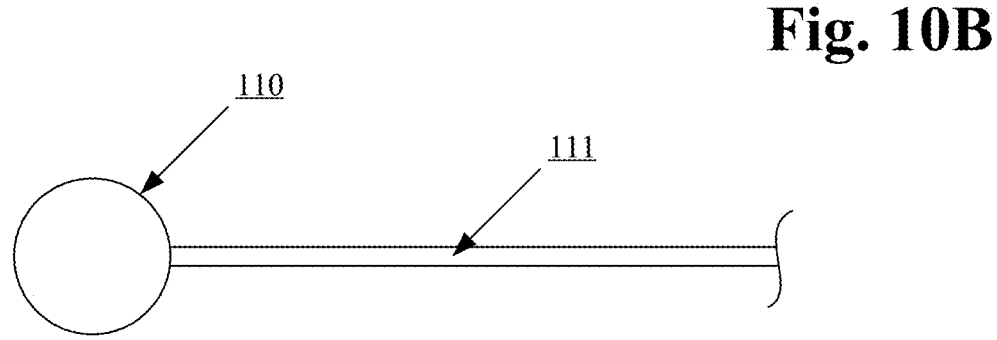
FIG. 10B is a diagram illustrating an embodiment of an intravenous or intraurethral ultrasound transmit-only probe carrying a convex apparent point-source transmit transducer.

In some embodiments, a transmit transducer 110 may be mounted to a distal end of an elongate catheter body 111 sized and configured to be positioned within a body cavity or lumen as shown for example in FIG. 10B. A catheter 111 and transmit transducer 110 designed for insertion into an artery, vein or the urethra may be severely limited in the number of wires that may be accommodated in order to keep a cable sufficiently small. However, only two wires may be necessary to activate a single apparent point-source transmitter. Such an intracavity apparent point-source transmitter may be positioned inside a patient's body close to an organ of interest so that the total path length from transmitter to scatterer and to one or more receive transducer arrays on the surface of the patient's skin may be reduced. This may cause attenuation of the signal to be reduced, thereby allowing for the use of higher ultrasound frequencies. In other embodiments, more than one apparent point-source transducer may be placed on the same catheter. In some embodiments, apparent point-source transmitter configured to be positioned within a body cavity may have a shape of nearly a complete sphere except for a point of attachment to a positioning catheter and access for an electrical connection on the inner surface.

Various methods may be used for triangulating the position of a transmit transducer relative to one or more receive transducers. For example, U.S. Pat. No. 8,473,239, which is incorporated herein by reference, provides a method for triangulating the position of a transducer element transmitting an ultrasound pulse based on the time-of-flight of a signal received by two or more receive elements located a known distance from one another. Similar techniques may be used to determine a location of one or more apparent point-source transmitters relative to one or more mechanically independent receive arrays. For example, an ultrasound ping transmitted from apparent point-source transmit transducer located on an intra-cavity probe positioned within a patient may be received with three or more elements of a receive array (or elements of separate receive arrays) positioned on the surface of the patient's skin at precisely known distances to one another.

When triangulating in three-dimensions, at least one of three of the receive elements should lie on a different plane than the remaining two. In other words, all receive elements should not lie in a common plane when triangulating the origin point of a three-dimensional ping.

The position of the apparent point-source transmitter may be triangulated based on the known position of the receive elements relative to one another and the difference between the time for the ping to reach the first receive element, the time for the ping to reach the second receive element, and the time for the ping to reach the third (and/or subsequent) receive element. In various embodiments, the time-of-flight values used for position measurements may be adjusted as described above in order to determine the location of the apparent point-source (i.e., the spherical center point) rather than the convex or concave transducer surface.

In some embodiments, using the position calculation method described above (or any other method), an imaging system with mechanically independent transmit and receive transducers may be configured to perform a transmitter-locating step while imaging. In some embodiments, the system may transmit a separate locating ping prior to transmitting one or more imaging pings. The position of the transmitter relative to the one or more receiver arrays may be determined and used in beamforming calculations for the echoes resulting from the one or more imaging pings following the locating ping. In some embodiments, locating pings may be transmitted at a different frequency than imaging pings.

In other embodiments, signals received directly from the imaging pings may be used to locate the transmitter relative to the one or more receiver arrays. In such embodiments, an initial peak of each transmitted imaging ping may be received at two or more receive elements at known positions relative to one another, and the position of the transmitter relative to the receive elements may be calculated as described above.

Figure 11:
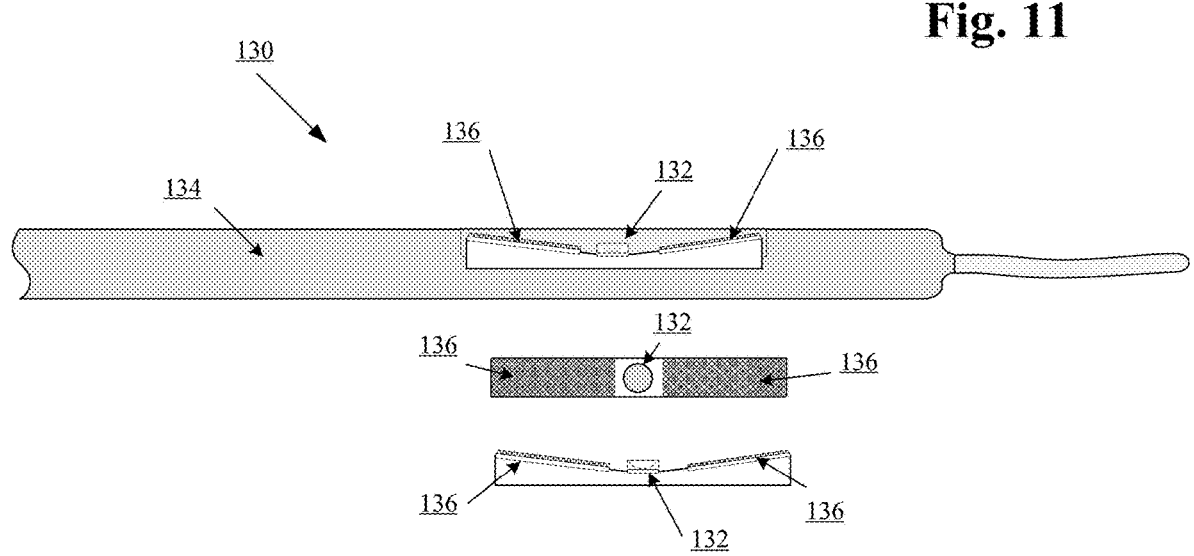
FIG. 11 is a cross-sectional view of an alternative embodiment of an intravenous ultrasound imaging probe carrying a concave apparent point-source transmit transducer and receive arrays.
Figure 11A:
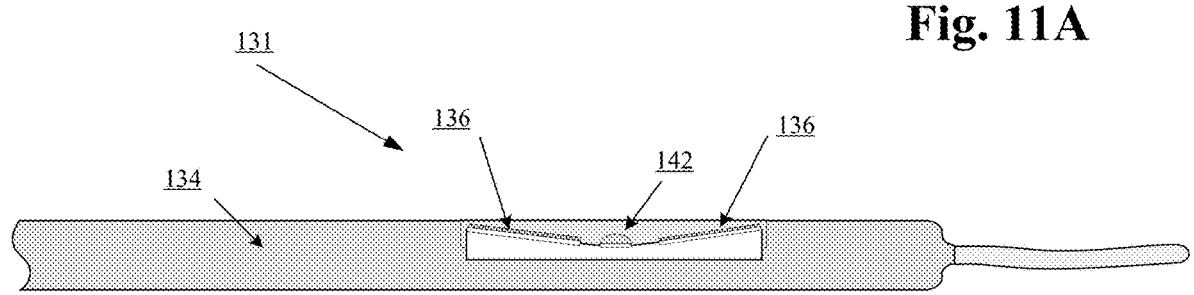
FIG. 11A is a cross-sectional view of an alternative embodiment of an intravenous ultrasound imaging probe carrying a convex apparent point-source transmit transducer and receive arrays.

FIG. 11 illustrates an alternative embodiment of an intravenous ultrasound probe 130 carrying a concave spherical-section apparent point-source transducer 132. The probe 130 may be built into a housing 134 mounted to a catheter or endoscope sized and configured for insertion into a bodily lumen such as a blood vessel, an esophagus, etc. The probe 130 may also include one, two or more receive arrays 136 arranged to receive echoes of three-dimensional ping signals transmitted by the apparent point-source transmitter 132. The receive arrays 136 may include any number of rectangular, square, circular, polygonal or otherwise-shaped transducer elements. In some cases, the receive arrays 136 may be angled towards the apparent point transducer 132. Alternatively, the receive arrays 136 may lie in a common plane with one another, or may be otherwise oriented. Alternatively, the receive arrays 136 may have a non-planar surface, such as convex or concaved curved surfaces. FIG. 11A illustrates an embodiment of a probe 131 that is substantially similar to the probe 130 of FIG. 11, but with a convex spherical section apparent point-source transmit transducer 142.

In some cases, all elements or arrays of a probe may be formed on a common substrate (e.g., using machining, molding, additive manufacturing, CMUT or other methods), while in other embodiments, apparent point-source and other arrays and/or elements may be made individually and assembled into a common probe structure using various other assembly methods.

Any 2D or 3D probe to be used for ping-based multiple aperture ultrasound imaging should be constructed and calibrated so as to record position information sufficient to define the actual acoustic position of each transducer element of the probe relative to a common coordinate system. Examples of systems and methods for aligning transducers during construction and for detecting the position of transducer elements are shown and described in Applicants' prior applications referenced above.

In some embodiments, apparent point-source transducers may be electrically connected within a probe so as to perform only transmit functions. In other embodiments, apparent point-source transducers may also be used to receive echoes by including a TX/RX switch.

Multiple Aperture Beamforming in 3D

Pings produced with apparent point-source transmit transducers may work particularly well with multiple aperture imaging, since echoes of the wide spherical-section 3D wavefront pulse may be received by multiple receivers over a wide area, much wider than any maximum coherence width of an imaged object with a non-homogeneous material. Beamforming during 3D ping-based multiple aperture imaging may involve calculating the locus of points corresponding to a time-of-flight of each received echo sample. In the case of 3D imaging, such a set of points is an ellipsoid—a three-dimensional elliptical surface having two focal points. One of the focal points is the position of the element on which the echo sample is received, and the other focal point is the position of the source from which the ping pulse was transmitted. In the case of apparent point-source transmitter transducer, the apparent transmit point used in such beamforming calculations is the center point of the spherical-cap shaped transducer forming the apparent point-source transmitter.

In some embodiments, ping-based multiple aperture imaging may operate by transmitting a spherical-section ultrasound ping signal from a first apparent point-source transmit transducer and receiving echoes with elements of two or more receive apertures. A complete "sub-image" may be formed by a controller or control system from echoes of a single ping received by a single receive element by triangulating the position of scatterers based on delay times between ping transmission and echo reception and the known three-dimensional positions of the transmit point and the receive point.

When using apparent point-source transducers, a time-of-transmit used in beamforming calculations may be substantially different from the time an electrical pulse is sent to the transducer. Because the sound waves do not actually originate from the apparent point-source (even though calculations are performed as if they do), the ping-transmit time used in beamforming calculations should be adjusted from the actual known value to an "apparent" value, corresponding to the time at which an outgoing waveform would appear to have been transmitted had it actually originated at the apparent point-source.

In the case of dome-shaped apparent point-source transducers, the transmitted ping start time may be adjusted by effectively adding an adjustment factor to each received echo time. In some embodiments, the adjustment time to be added may be a time value equal to the time required for a sound wave to travel from the spherical center to the convex outer transducer surface at a chosen speed of sound. In some embodiments, the chosen speed of sound for such an adjustment may be the same speed of sound used by an imaging system as the speed-of-sound in the object being imaged. In other embodiments, the chosen speed of sound for a convex apparent point-source adjustment may be the speed-of-sound in a stand-off or acoustic gel material immediately adjacent the transducer surface.

In the case of concave bowl-shaped apparent point-source transducers, the transmitted ping start time may be adjusted by effectively subtracting an adjustment factor from each received echo time. In some embodiments, the adjustment time to be subtracted may be a time value equal to the time required for a sound wave to travel from the inner concave transducer surface to the spherical center at a chosen speed of sound. In some embodiments, the chosen speed of sound for such an adjustment may be the same speed of sound used by an imaging system as the speed-of-sound in the object being imaged. In other embodiments, the chosen speed of sound for a concave apparent point-source adjustment may be the speed-of-sound in a stand-off or acoustic gel material immediately adjacent the transducer surface. In other embodiments, instead of subtracting time from each calculation, the adjustment may be calculated in terms of a number of data samples (e.g., based on a known sample rate), and an appropriate number of data samples at the beginning of a group of received echoes may be omitted from the beamforming calculation for each ping transmitted from a concave apparent point-source transmitter.

Images obtained from different unique combinations of one ping and one receive aperture may be referred to herein as "sub-image layers." Multiple sub-image layers may be combined coherently to improve overall image quality. Additional image layer combining may be performed to further improve the quality of a final image. In the context of image layer combining, the term "image" may refer to a single two-dimensional pixel, a single voxel of a three-dimensional volume or a collection of any number of pixels or voxels.

Image layer combining may be described in terms of three image layer levels. These three cases include first-level image layers, second-level image layers and third-level image layers. (1) A first-level image layer may be formed from echoes received at a single receive aperture resulting from a single ping from a single transmit aperture (where a "transmit aperture" can be a single apparent point-source transmit element, a single small-element transmitter, or a group of transmit elements). For a unique combination of a single ping and a single receive aperture, the delayed echoes received by all the receive elements in the receive aperture may be summed coherently to obtain a first-level image layer. (2) Multiple first-level image layers resulting from echoes of multiple transmit pings (from the same or different transmit apertures) received at a single receive aperture can be summed together to produce a second-level image layer. Second-level image layers may be further processed to improve alignment or other image characteristics. (3) Third-level images may be obtained by combining second-level image layers formed with data from multiple receive apertures. In some embodiments, third-level images may be displayed as sequential time-domain frames to form a moving image.

In some embodiments, pixels or voxels of a first-level image layer may also be formed by summing in-phase and quadrature echo data, that is by summing each echo with an echo ¼ wavelength delayed for each receive-aperture element. In some cases, echo data may be sampled and stored as an in-phase data set and as a separate quadrature data set. In other cases, if the digital sampling rate is divisible by four, then a quadrature sample corresponding to an in-phase sample may be identified by selecting a sample at an appropriate number of samples prior to the in-phase sample. If the desired quadrature sample does not correspond to an existing whole sample, a quadrature sample may be obtained by interpolation. Combining in-phase and quadrature data for a single image (pixel, voxel or collection of pixels or voxels) may provide the advantage of increasing the resolution of the echo data without introducing blurring effects. Similarly, samples at values other than ¼ wavelength may be combined with in-phase samples in order to improve various imaging characteristics.

Combination, summation or averaging of various image layers may be accomplished either by coherent addition, incoherent addition, or a combination of the two. Coherent addition (incorporating both phase and magnitude information during image layer summation) tends to maximize lateral resolution, whereas incoherent addition (summing magnitudes only and omitting phase information) tends to average out speckle noise and minimize the effects of image layer alignment errors that may be caused by minor variations in the speed of sound through the imaged medium. Speckle noise is reduced through incoherent summing because each image layer will tend to develop its own independent speckle pattern, and summing the patterns incoherently has the effect of averaging out these speckle patterns. Alternatively, if the patterns are added coherently, they reinforce each other and only one strong speckle pattern results. Incoherent addition may be thought of as akin to instantaneous compound imaging, which has long been known as a means to suppress speckle noise.

In most embodiments, echoes received by elements of a single receive aperture are typically combined coherently. In some embodiments, the number of receive apertures and/or the size of each receive aperture may be changed in order to maximize some desired combination of image quality metrics such as lateral resolution, speed-of-sound variation tolerance, speckle noise reduction, etc. In some embodiments, such alternative element-to-aperture grouping arrangements may be selectable by a user. In other embodiments, such arrangements may be automatically selected or developed by an imaging system.

Variations in the speed of sound may be tolerated by incoherent addition as follows: Summing two pixels coherently with a speed-of-sound variation resulting in only half a wavelength's delay (e.g., approximately 0.25 mm for a 3 MHz probe) results in destructive phase cancellation, which causes significant image data loss; if the pixels are added incoherently, the same or even greater delay causes only an insignificant spatial distortion in the image layer and no loss of image data. The incoherent addition of such image layers may result in some smoothing of the final image (in some embodiments, such smoothing may be added intentionally to make the image more readable).

At all three image layer levels, coherent addition can lead to maximum lateral resolution of a multiple aperture system if the geometry of the probe elements is known to a desired degree of precision and the assumption of a constant speed of sound across all paths is valid. Likewise, at all image layer levels, incoherent addition leads to the best averaging out of speckle noise and tolerance of minor variations in speed of sound through the imaged medium.

In some embodiments, coherent addition can be used to combine image layers resulting from apertures for which phase cancellation is not likely to be a problem, and incoherent addition can then be used where phase cancellation would be more likely to present a problem, such as when combining images formed from echoes received at different receive apertures separated by a distance exceeding some threshold.

In some embodiments, all first-level images may be formed by using coherent addition of all sub-image layers obtained from elements of a common receive aperture, assuming the receive aperture has a width less than the maximum coherent aperture width. For second and third level image layers, many combinations of coherent and incoherent summation are possible. For example, in some embodiments, second-level image layers may be formed by coherently summing contributing first-level image layers, while third-level image layers may be formed by incoherent summing of the contributing second-level image layers.

Time-domain frames may be formed by any level of image layer depending on the desired trade-off between processing time and image quality. Higher-level images will tend to be of higher quality, but may also require more processing time. Thus, if it is desired to provide real-time imaging, the level of image layer combination processing may be limited in order to display images without significant "lag" being visible to the operator. The details of such a trade-off will depend on the particular processing hardware in use as well as other factors.

Figure 12:
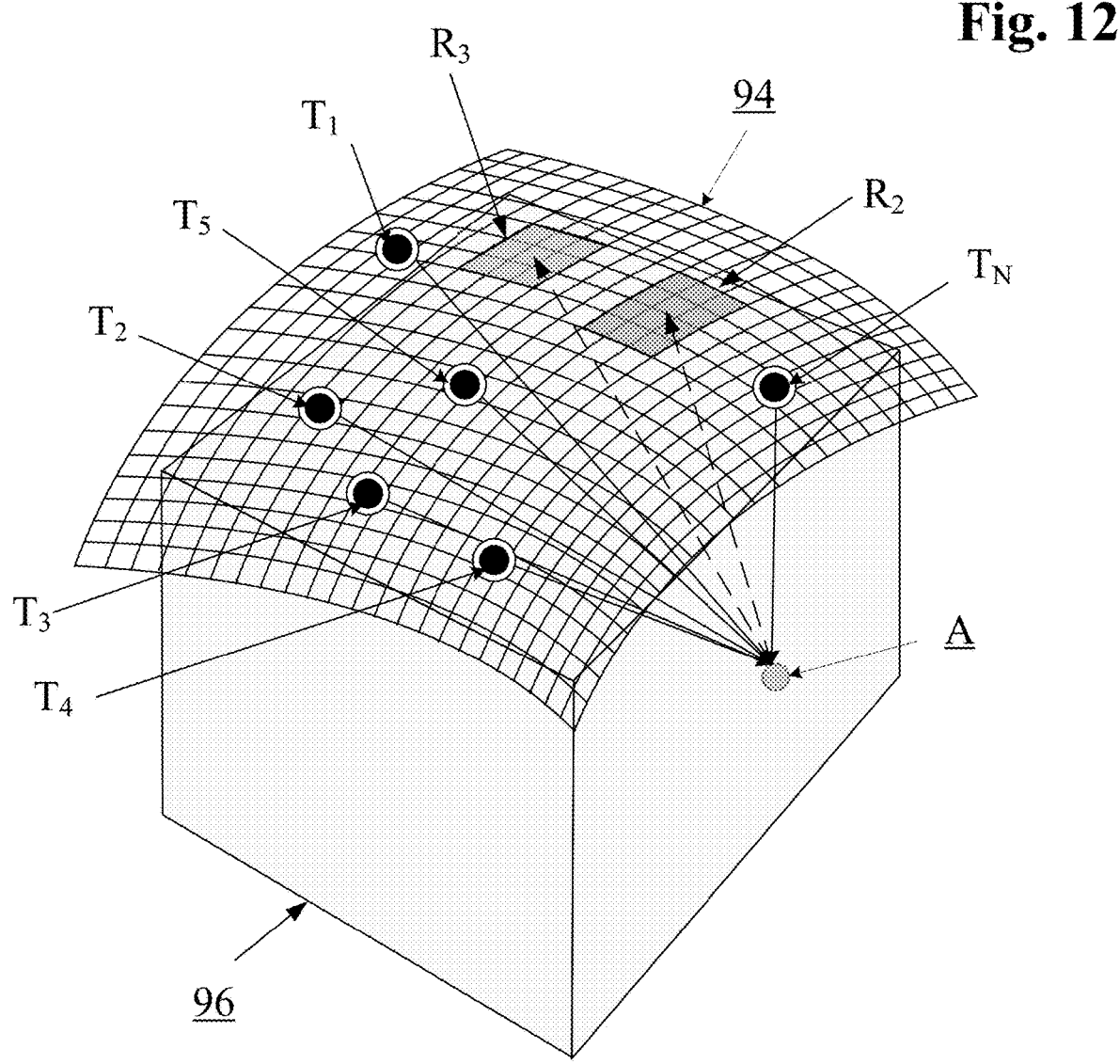
FIG. 12 is a schematic perspective view illustrating an embodiment of a continuous transducer array including a plurality of apparent point-source transmit elements and a target object to be imaged.

An example may be understood with reference to FIG. 12, which schematically illustrates a continuous curved transducer array 91 including a plurality of apparent point-source transmit transducers $T_1$-$T_n$ within an array of small transducer elements 94 positioned above an object 96 to be imaged. Receive apertures $R_2$ and $R_3$ are defined as groups of small transducer elements. In various embodiments, any group of transducer elements may be defined as a receive aperture.

In use, a 3D ping in the form of a spherical-section wavefront (e.g., a perfectly hemispherical wavefront, or a wavefront with a shape greater or less than a hemisphere) may be transmitted from apparent point-source transmit transducer (e.g., T1). The wavefront may travel into the object 96 and may be reflected by a reflector such as that shown at point A. Reflected ultrasound signals may then be received by the elements of a receive aperture (e.g., elements $R_{2,1}$ through $R_{2,n}$ of receive aperture $R_2$). Three-dimensional echo data may be collected by receiving echoes with receive apertures that do not lie on a common plane with each other and/or with the transmit aperture. For example, each of receive apertures $R_1$ and $R_2$ comprise elements that are spaced from one another in at least two dimensions relative to the imaged object 96 and thus the receive apertures $R_1$ and $R_2$ do not lie on the same plane as one another, nor on a common plane with the transmit aperture T1. Thus, in some embodiments, echoes may be received by all receive elements, and those elements may be grouped into apertures based on factors such as position and maximum coherence width.

The echo sample corresponding to point A may then be beamformed to determine the possible location of point A within the object 96. Beamforming may proceed by calculating a locus of possible positions for point A based on the known transmit time, the known echo receive time, the known location of a receive element (e.g., element $R_{2,1}$ of receive aperture $R_2$) and the known location of the apparent point-source (i.e., the spherical center of transmit element $T_1$ in this example). The same calculation may be performed for echoes received at the remaining receive elements of the same receive aperture, each receive element defining a slightly different ellipsoid. The information from all of the receive elements may then be combined (e.g., coherently as described above) in order to converge on a small three-dimensional estimate of the location of point A. The same process may then be repeated for echo samples of point A received by elements of a second (or more) receive aperture from the same transmitted ping. Similarly, the same process may be repeated for a second (or more) 3D pings transmitted from the same or different transmit elements.

Because a high-quality 3D image may be obtained from echoes of a single transmitted ping using the above procedure, a ping-based multiple aperture imaging system with apparent point-source transmitters may be used for performing 4D imaging to display a real-time 3D video of a moving object.

Similarly, 3D pings transmitted from apparent point-source transmitter may also be used for ping-based multiple aperture Doppler, multiple aperture elastography or any other imaging technique that may benefit from high-frame-rate 3D imaging.

2D Imaging while Collecting 3D Data

In some embodiments, a form of 2D imaging may be performed using a probe configured for 3D imaging by simply beamforming and displaying only a 2D slice of received echo data from the received three-dimensional echo data. For example, such techniques may be used in order to reduce a beamform calculation and simplify display for real-time imaging using an imaging device with limited processing capability, while still retaining the full 3D echo data. The full 3D echo data may be beamformed and reviewed at a later time using a device with greater processing power. In some embodiments, the 2D slice to be beamformed and displayed may be automatically selected by an imaging device. Alternatively, the 2D slice to be beamformed and displayed may be selected or adjusted by an operator of the device.

Apparent Source for 2D Planar Imaging

Figure 13:
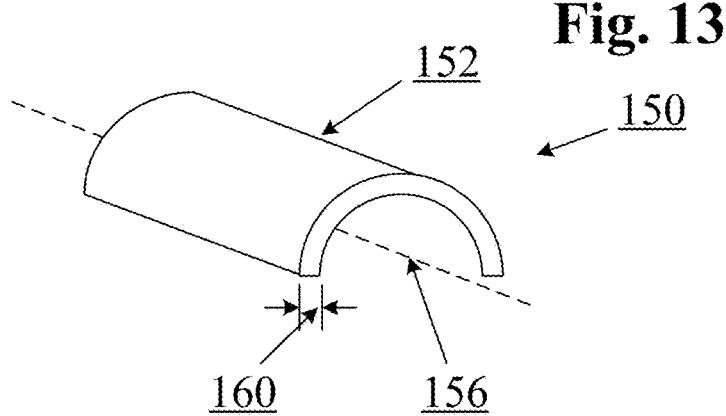
FIG. 13 is a schematic illustration of apparent source transducer configured for transmitting ultrasound signals substantially confined to a single imaging plane.

In some embodiments, apparent source transmit transducer may be configured specifically for 2D planar imaging. While apparent point-source transmitter as described above will transmit ultrasound in three dimensions, a 2D apparent source transducer may be configured to transmit ultrasound signals that are confined to a single plane (or at least with minimal "leakage" out of the image plane). In some embodiments, such a 2D apparent source transducer 150 may have a shape of a shell 152 with a cylindrical section shape such as that shown in FIG. 13. Such a cylindrical section shell transducer 150 may be arranged in a probe such that the longitudinal axis 156 of the cylindrical section is perpendicular to the imaging plane. As a result, the longitudinal axis 156 of the cylindrical section shell 156 intersects the image plane at a point. That intersection point may be used as apparent point-source in beamforming calculations for echoes of pings transmitted from a 2D apparent source transducer 150.

As with the spherical-section transducers described above, cylindrical section transducers 150 may be made in various shapes, sizes, and circular cross-sections as needed (the description of FIG. 2A-FIG. 2C may be extended to the cylindrical-section case). In particular, a cylindrical-section transducer may be constructed with circular radii in similar ranges as the ranges of spherical radii described above. The cylindrical section may also be formed with a range of cut elevations depending on the needs of a particular application. A cylindrical shell transducer 150 may also be formed with a shell thickness 160 selected for the needs of a particular application as described above with respect to spherical cap shells.

A cylindrical-section transducer 150 may also be configured such that ultrasound signals are transmitted into an imaged medium from either the convex surface or the concave surface. In various embodiments, a probe including a cylindrical section transducer 150 may include a focusing lens configured to focus transmitted ultrasound energy in the imaging plane. In use, time adjustments may be made to treat the cylindrical centerline (i.e., the circular center of the sphere) as the mathematical origin of pings transmitted from such a transducer.

In various embodiments, receive elements may also be formed from cylindrical section shell structures. Receive elements may typically have substantially smaller transducer surface areas, since echoes received by many receive transducers may be combined into to increase the received echo signal.

Multiple Aperture Ultrasound Imaging System Components

Figure 14:
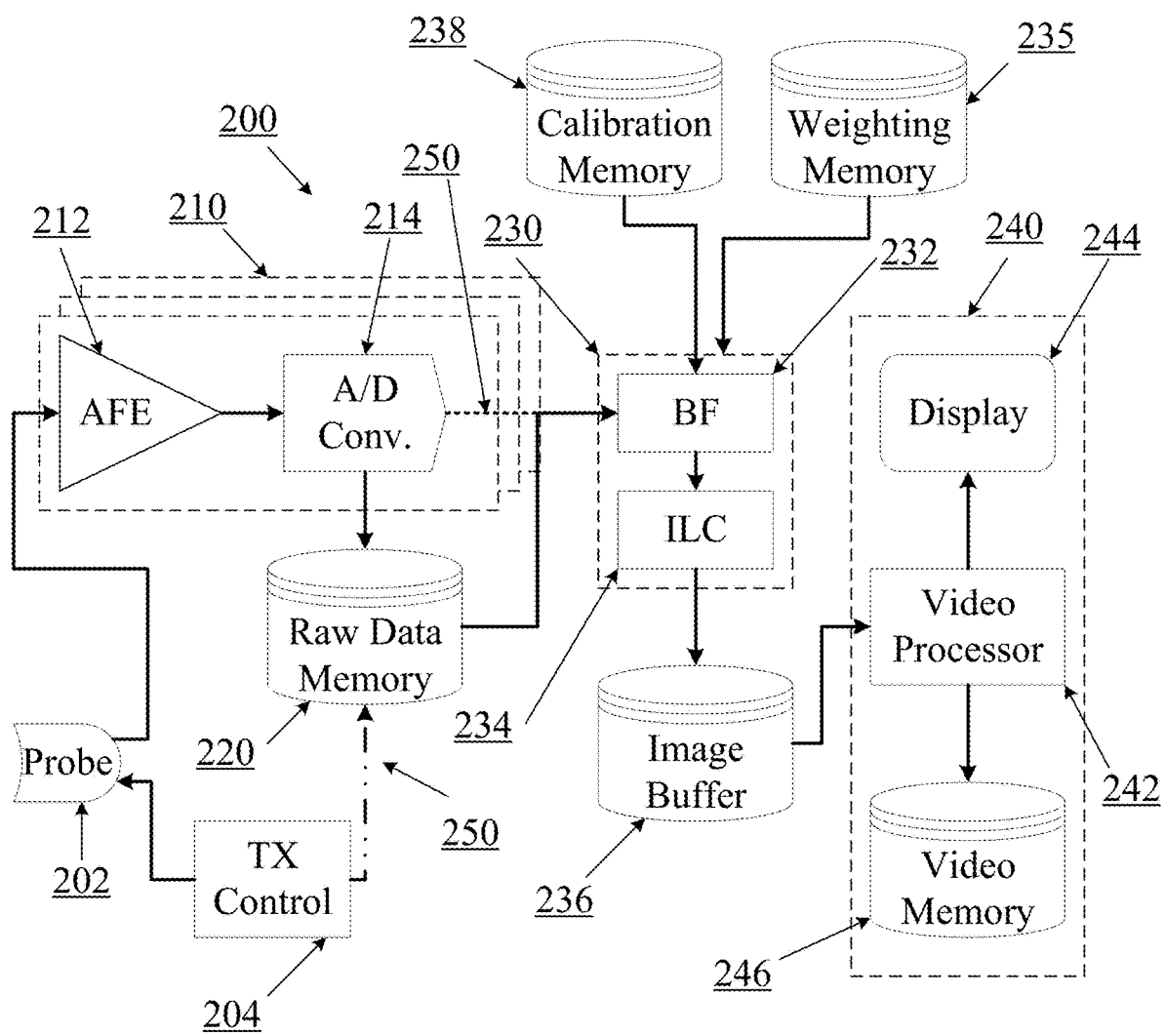
FIG. 14 is a schematic view illustrating an embodiment of a multiple aperture imaging system.

The block diagram of FIG. 14 illustrates components of an ultrasound imaging system 200 that may be used in combination with various embodiments of systems and methods as described herein. The system 200 of FIG. 14 may include several subsystems: a transmit control subsystem 204, a probe subsystem 202, a receive subsystem 210, an image generation subsystem 230, and a video subsystem 240. In various embodiments, the system 200 may also include one or more memory devices for containing various data for use during one or more ultrasound imaging steps. Such memory devices may include a raw echo data memory 220, a weighting factor memory 235, a calibration data memory 238, an image buffer 236 and/or a video memory 246. In various embodiments all data (including software and/or firmware code for executing any other process) may be stored on a single memory device. Alternatively, separate memory devices may be used for one or more data types. Further, any of the modules or components represented in FIG. 2B may be implemented using any suitable combination of electronic hardware, firmware and/or software.

The transmission of ultrasound signals from elements of the probe 202 may be controlled by a transmit control subsystem 204. In some embodiments, the transmit control subsystem 204 may include any combination of analog and digital components for controlling transducer elements of the probe 202 to transmit un-focused ultrasound pings at desired frequencies and intervals from selected transmit apertures according to a desired imaging algorithm. In some embodiments a transmit control system 204 may be configured to transmit ultrasound pings at a range of ultrasound frequencies. In some (though not all) embodiments, the transmit control subsystem may also be configured to control the probe in a phased array mode, transmitting focused (i.e., transmit beamformed) ultrasound scanline beams.

In some embodiments, a transmit control sub-system 204 may include a transmit signal definition module 206 and a transmit element control module 208. The transmit signal definition module 206 may include suitable combinations of hardware, firmware and/or software configured to define desired characteristics of a signal to be transmitted by an ultrasound probe. For example, the transmit signal definition module 206 may establish (e.g., based on user inputs or on predetermined factors) characteristics of an ultrasound signal to be transmitted such as a pulse start time, pulse length (duration), ultrasound frequency, pulse power, pulse shape, pulse direction (if any), pulse amplitude, transmit aperture location, or any other characteristics.

The transmit element control module 208 may then take information about the desired transmit pulse and determine the corresponding electrical signals to be sent to the appropriate transducer elements in order to produce this signal. In various embodiments, the signal definition module 206 and the transmit element control module 208 may comprise separate electronic components, or may include portions of one or more common components.

Upon receiving echoes of transmitted signals from a region of interest, the probe elements may generate time-varying electrical signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214. In some embodiments, each channel of the receive subsystem 210 may also include digital filters and data conditioners (not shown) after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some pre-determined sampling rate. Unlike most ultrasound systems, some embodiments of the ultrasound imaging system of FIG. 14 may then store digital data representing the timing, phase, magnitude and/or the frequency of ultrasound echo signals received by each individual receive element in a raw data memory device 220 before performing any further receive beamforming, filtering, image layer combining or other image processing.

In order to convert the captured digital samples into an image, the data may be retrieved from the raw data memory 220 by an image generation subsystem 230. As shown, the image generation subsystem 230 may include a beamforming block 232 and an image layer combining ("ILC") block 234. In some embodiments, a beamformer 232 may be in communication with a calibration memory 238 that contains probe calibration data. Probe calibration data may include information about the precise position, operational quality, and/or other information about individual probe transducer elements. The calibration memory 238 may be physically located within the probe, within the imaging system, or in location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g., as referred to in the art as a "cine loop".

In some embodiments, the AFE 212 may be configured to perform various amplification and filtering processes to a received analog signal before passing the analog signal to an analog-to-digital conversion device. For example, an AFE 212 may include amplifiers such as a low noise amplifier (LNA), a variable gain amplifier (VGA), a bandpass or lowpass/anti-aliasing filter, and/or other amplification or filtering devices. In some embodiments, an AFE device 212 may be configured to begin passing an analog signal to an ADC 214 upon receiving a trigger signal. In other embodiments, an AFE device can be "free running", continuously passing an analog signal to an ADC.

In some embodiments, each analog-to-digital converter 214 may generally include any device configured to sample a received analog signal at some consistent, predetermined sampling rate. For example, in some embodiments, an analog-to-digital converter may be configured to record digital samples of a time-varying analog signal at 25 MHz, which is 25 million samples per second or one sample every 40 nanoseconds. Thus, data sampled by an ADC may simply include a list of data points, each of which may correspond to a signal value at a particular instant. In some embodiments, an ADC 214 may be configured to begin digitally sampling an analog signal upon receiving a trigger signal. In other embodiments, an ADC device can be "free running", continuously sampling a received analog signal.

In some embodiments, the raw data memory device 220 may include any suitable volatile or non-volatile digital memory storage device. In some embodiments, the raw data memory 220 may also comprise communication electronics for transmitting raw digital ultrasound data to an external device over a wired or wireless network. In such cases, the transmitted raw echo data may be stored on the external device in any desired format. In other embodiments, the raw data memory 220 may include a combination of volatile memory, non-volatile memory and communication electronics.

In some embodiments, the raw data memory device 220 may comprise a temporary (volatile or non-volatile) memory section, and a long-term non-volatile memory section. In an example of such embodiments, the temporary memory may act as a buffer between the ADC 214 and the beamformer 232 in cases where the beamformer 232 may be unable to operate fast enough to accommodate data at the full rate from the ADC 214. In some embodiments, a long-term non-volatile memory device may be configured to receive data from a temporary memory device or directly from the ADC 214. Such a long-term memory device may be configured to store a quantity of raw echo data for subsequent processing, analysis or transmission to an external device.

In some embodiments, the beamforming block 232 and the image layer combining block 234 may each include any digital signal processing and/or computing components configured to perform the specified processes (e.g., as described below). For example, in various embodiments the beamforming 232 and image layer combining 234 may be performed by software running on a single GPU, on multiple GPUs, on one or more CPUs, on combinations of CPUs & GPUs, on single or multiple accelerator cards or modules, on a distributed processing system, or a clustered processing system. Alternatively, these or other processes may be performed by firmware running on an FPGA (Field Programmable Gate Array) architecture or one or more dedicated ASIC (Application-Specific Integrated Circuit) devices.

In some embodiments, the video processor 242 may include any video processing hardware, firmware and software components that may be configured to assemble image frames into a video stream for display and/or storage.

Data Capture & Offline Analysis

In various embodiments, raw un-beamformed echo data resulting from a ping transmitted from apparent point-source transmit transducer and received by one or more arrays of receive transducer elements may be captured and stored in a raw data memory device for subsequent retrieval and analysis. In addition to such echo data, additional data may also be stored and/or transmitted over a network and retrieved for subsequent image generation and analysis. Such additional data may include calibration data describing the positions of the transmitting and receiving transducer elements, and transmit data describing the identity (or position) of transmitting transducers associated with specific echo data.

After retrieving such data, a clinician may use the data to reconstruct imaging sessions in a variety of ways while making adjustments that may not have been made during a live imaging session. For example, images of a series of 2D slices through the 3D volume may be generated and shown in succession in order to simulate a 2D transducer passing across a surface of the region of interest. Examples of such methods are described in Applicant's co-pending U.S. patent application Ser. No. 13/971,689 filed Aug. 20, 2013, which is incorporated herein by reference.

Some embodiments of a probe configured for imaging an entire patient's body or a substantial portion of a patient's body may comprise an array of apparent point-source transmitters and receive elements sized to cover a substantial portion of the desired region of a patient's body. For example, a probe may be sized to cover substantially half of a patient's chest or more. Such a probe may have a maximum dimension of about 8 cm to about 10 cm.

Alternatively, a much smaller probe capable of insonifying a conically-shaped volume of, for example, + or −30 degrees, can be placed on a patient's body such that an organ of interest may be included in the cone. Such a probe may be placed in more than one place to cover a larger volume of interest.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. Also as used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. An ultrasound imaging system comprising:
   a first apparent point-source transmit transducer shaped as a spherical section having a spherical center point, the first apparent point-source transmit transducer configured to transmit a three-dimensional semi-spherical pulse into a target object to be imaged;
   a first plurality of receive transducer elements configured to receive echoes of the three-dimensional semi-spherical pulse;
   a second plurality of receive transducer elements configured to receive echoes of the three-dimensional semi-spherical pulse;
   a computing system configured to control transmission of the three-dimensional semi-spherical pulse and to determine a position of reflectors within the object based on a known position of the spherical center point of the apparent point-source transmit transducer, known positions of the elements of the first and second pluralities of receive transducer elements, a time at which the three-dimensional semi-spherical pulse was transmitted, and times at which the echoes are received, the computing system being further configured to calculate a total path distance as a sum of a first distance between the spherical center point and the target object and a second distance between the target object and the receive transducer element, wherein calculating the total path distance comprises adding an apparent path segment representing a distance from a convex transmit transducer surface of the apparent point-source transmit transducer to the spherical center point, and determining a locus of possible points at which the target object may lie.

2. The system of claim 1, wherein the first apparent point-source transmit transducer is shaped as a spherical section that is greater than half a sphere.

3. The system of claim 1, wherein the first apparent point-source transmit transducer is shaped as a spherical section that is less than half a sphere.

4. The system of claim 1, wherein the first apparent point-source transmit transducer is shaped as a spherical section that is half a sphere.

5. The system of claim 1, wherein the first apparent point-source transmit transducer has a spherical radius of between 0.2 mm and 10 mm.

6. The system of claim 1, wherein the first apparent point-source transmit transducer is configured to transmit ultrasound signals at a first frequency range.

7. The system of claim 6 further comprising a second apparent point-source transmit transducer with a spherical radius and configured to transmit ultrasound signals at a second frequency range, the second frequency range being different than the first frequency range.

8. The system of claim 1, wherein the first apparent point-source transmit transducer comprises a shell of piezoelectric material with a constant thickness.

9. The system of claim 1, wherein the apparent point-source transmit transducer comprises a shell having a constant-thickness made of a continuous piezoelectric material.

10. The system of claim 1, wherein the apparent point-source transmit transducer comprises a shell having a constant-thickness made of a segmented piezoelectric material.

11. The system of claim 1, wherein the apparent point-source transmit transducer comprises a plurality of segments arranged into the spherical shape, wherein all segments are configured to transmit ultrasound signals simultaneously.

12. The system of claim 1, further comprising a computer readable memory containing data describing a position of the spherical center point of the apparent point-source transmit transducer relative to at least one element of the first plurality of receive transducer elements.

13. The system of claim 1, further comprising a computer readable memory containing an adjustment factor representing apparent path segment equal to a distance from a surface of the first apparent point-source transmit transducer to the spherical center point.

* * * * *